(12) United States Patent
Buck et al.

(10) Patent No.: US 11,253,277 B2
(45) Date of Patent: *Feb. 22, 2022

(54) SYSTEMS FOR ACCESSING A CENTRAL PULMONARY ARTERY

(71) Applicant: Imperative Care, Inc., Campbell, CA (US)

(72) Inventors: Michael Buck, Menlo Park, CA (US); Julia Fox, San Carlos, CA (US); James Jacobs, Danville, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/125,743

(22) Filed: Dec. 17, 2020

(65) Prior Publication Data

US 2021/0186542 A1  Jun. 24, 2021

Related U.S. Application Data

(60) Provisional application No. 63/064,273, filed on Aug. 11, 2020, provisional application No. 62/950,058, filed on Dec. 18, 2019.

(51) Int. Cl.
*A61B 17/22* (2006.01)
*A61B 8/12* (2006.01)
(Continued)

(52) U.S. Cl.
CPC ............ *A61B 17/22* (2013.01); *A61B 5/0084* (2013.01); *A61B 8/12* (2013.01);
(Continued)

(58) Field of Classification Search
CPC .......... A61B 17/22031; A61B 17/3417; A61B 17/3498; A61B 2017/22034;
(Continued)

(56) References Cited

U.S. PATENT DOCUMENTS

| 4,030,503 A | 6/1977 | Clark, III |
| 4,319,580 A | 3/1982 | Colley et al. |

(Continued)

FOREIGN PATENT DOCUMENTS

| DE | 10 2010 053111 | 6/2012 |
| DE | 10 2012 112732 | 6/2014 |

(Continued)

OTHER PUBLICATIONS

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

(Continued)

*Primary Examiner* — Tan-Uyen T Ho
*Assistant Examiner* — Rachel S Highland
(74) *Attorney, Agent, or Firm* — Knobbe Martens Olson & Bear, LLP

(57) ABSTRACT

A system for accessing a central pulmonary artery includes an elongate, flexible tubular catheter, having a proximal end, a distal end and a catheter hub on the proximal end. An elongate, flexible rail has a proximal end, a distal end and a rail hub on the proximal end. The rail has a distal advance segment which extends at least about 10 cm beyond the distal end of the catheter when the catheter hub is adjacent the rail hub.

16 Claims, 20 Drawing Sheets

(51) Int. Cl.
    *A61B 5/00*         (2006.01)
    *A61B 17/34*       (2006.01)
    *A61M 25/01*       (2006.01)
    *A61M 25/09*       (2006.01)
    *A61B 17/221*      (2006.01)

(52) U.S. Cl.
    CPC .... *A61B 17/22031* (2013.01); *A61B 17/3417* (2013.01); *A61B 17/3498* (2013.01); *A61M 25/0138* (2013.01); *A61M 25/09* (2013.01); *A61B 2017/2217* (2013.01); *A61B 2017/22034* (2013.01); *A61B 2017/22038* (2013.01); *A61B 2017/22079* (2013.01); *A61B 2017/3458* (2013.01); *A61M 2025/0183* (2013.01); *A61M 2210/125* (2013.01)

(58) Field of Classification Search
    CPC .......... A61B 2017/3458; A61M 25/00; A61M 2025/0004; A61M 2025/0006; A61M 2025/0063; A61M 25/0097; A61M 25/01; A61M 25/0102; A61M 39/10; A61M 39/1011; A61M 2039/1016
    See application file for complete search history.

(56) References Cited

U.S. PATENT DOCUMENTS

| | | | |
|---|---|---|---|
| 4,611,594 A | 9/1986 | Grayhack et al. |
| 4,619,274 A | 10/1986 | Morrison et al. |
| 4,762,129 A | 8/1988 | Bonzel |
| 4,762,130 A | 8/1988 | Fogarty et al. |
| 4,810,582 A | 3/1989 | Gould et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,234,416 A | 8/1993 | Macaulay et al. |
| 5,243,997 A | 9/1993 | Uflacker |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,766,191 A | 6/1998 | Trerotola |
| 5,776,141 A | 7/1998 | Klein et al. |
| 5,827,242 A | 10/1998 | Follmer |
| 5,843,103 A | 12/1998 | Wulfman |
| 5,885,209 A | 3/1999 | Green |
| 5,891,114 A | 4/1999 | Chien et al. |
| 5,895,398 A | 4/1999 | Wensel |
| 5,899,892 A | 5/1999 | Mortier et al. |
| 5,916,192 A | 6/1999 | Nita et al. |
| 5,935,112 A | 8/1999 | Stevens |
| 5,938,645 A | 8/1999 | Gordon |
| 5,951,539 A | 9/1999 | Nita et al. |
| 6,007,530 A | 12/1999 | Dornhofer et al. |
| 6,059,745 A | 5/2000 | Gelbfish |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates |
| 6,197,014 B1 | 3/2001 | Samson et al. |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal |
| 6,355,027 B1 | 3/2002 | Le et al. |
| 6,394,976 B1 | 5/2002 | Winston et al. |
| 6,451,036 B1 | 6/2002 | Heitzmann |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth |
| 6,524,303 B1 | 2/2003 | Garibaldi et al. |
| 6,520,934 B1 | 3/2003 | Lee |
| 6,533,751 B2 | 3/2003 | Cragg |
| 6,554,820 B1 | 4/2003 | Wendlandt |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,666,874 B2 | 12/2003 | Heitzmann |
| 6,669,670 B1 | 12/2003 | Muni et al. |
| 6,719,717 B1 | 4/2004 | Johnson et al. |
| 6,776,770 B1 | 8/2004 | Trerotola |
| 6,805,692 B2 | 10/2004 | Muni et al. |
| 6,824,550 B1 | 11/2004 | Pintor et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas |
| 7,037,267 B1 | 5/2006 | Lipson et al. |
| 7,104,979 B2 | 9/2006 | Jansen et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas |
| 7,229,461 B2 | 6/2007 | Chin et al. |
| 7,232,452 B2 | 6/2007 | Adams et al. |
| 7,235,088 B2 | 6/2007 | Pintor et al. |
| 7,250,042 B2 | 7/2007 | Kataishi et al. |
| 7,309,334 B2 | 12/2007 | von Hoffmann |
| 7,335,216 B2 | 2/2008 | Bender |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,713,227 B2 | 5/2010 | Wholey et al. |
| 7,771,358 B2 | 8/2010 | Moehring et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin |
| 7,905,891 B2 | 3/2011 | Self |
| 7,931,659 B2 | 4/2011 | Bose et al. |
| 7,938,820 B2 | 5/2011 | Webster et al. |
| 7,947,012 B2 | 5/2011 | Spurchise et al. |
| 7,988,646 B2 | 8/2011 | Taber |
| 8,021,351 B2 | 9/2011 | Boldenow et al. |
| 8,048,032 B2 | 11/2011 | Root et al. |
| 8,057,497 B1 | 11/2011 | Raju et al. |
| 8,062,316 B2 | 11/2011 | Patel |
| 8,070,694 B2 | 12/2011 | Galdonik et al. |
| 8,084,246 B2 | 12/2011 | Hoon et al. |
| 8,142,413 B2 | 3/2012 | Root et al. |
| 8,114,032 B2 | 4/2012 | Ferry et al. |
| 8,157,792 B2 | 4/2012 | Dolliver et al. |

(56) References Cited

U.S. PATENT DOCUMENTS

| | | |
|---|---|---|
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,308,655 B2 | 11/2012 | Grigoryants |
| 8,361,095 B2 | 1/2013 | Osborne |
| 8,366,735 B2 | 2/2013 | Bose et al. |
| 8,460,312 B2 | 6/2013 | Bose et al. |
| 8,517,955 B2 | 8/2013 | Keast |
| 8,535,293 B2 | 9/2013 | Faherty et al. |
| 8,608,754 B2 | 12/2013 | Wensel et al. |
| 8,609,426 B2 | 12/2013 | Silver |
| 8,663,259 B2 | 3/2014 | Levine et al. |
| 8,682,411 B2 | 3/2014 | Kassab et al. |
| 8,696,698 B2 | 4/2014 | Chomas |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse |
| 8,876,854 B2 | 11/2014 | Christiansen et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,998,946 B2 | 4/2015 | Morero et al. |
| 9,014,786 B2 | 4/2015 | Carmeli et al. |
| 9,017,309 B2 | 4/2015 | Tanikawa et al. |
| 9,023,070 B2 | 5/2015 | Levine et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,421,328 B2 | 8/2016 | Brueckner et al. |
| 9,439,791 B2 | 9/2016 | Vong et al. |
| 9,451,884 B2 | 9/2016 | Palovich |
| 9,451,963 B2 | 9/2016 | Cruise et al. |
| 9,463,006 B2 | 10/2016 | Forde et al. |
| 9,480,813 B2 | 11/2016 | Fukuoka et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,717,500 B2 | 8/2017 | Tieu et al. |
| 9,724,103 B2 | 8/2017 | Cruise et al. |
| 9,764,111 B2 | 9/2017 | Gulachenski |
| 9,770,251 B2 | 9/2017 | Bowman et al. |
| 9,775,730 B1 | 10/2017 | Waltzman |
| 9,789,242 B2 | 10/2017 | Criado et al. |
| 9,789,283 B2 | 10/2017 | Richter et al. |
| 9,801,643 B2 | 10/2017 | Hansen et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,878,076 B2 | 1/2018 | Gülcher et al. |
| 9,883,885 B2 | 2/2018 | Hendrick et al. |
| 9,907,880 B2 | 3/2018 | Cruise et al. |
| 9,987,028 B2 | 6/2018 | Lowinger et al. |
| 9,999,355 B2 | 6/2018 | Kirenko |
| 10,028,854 B2 | 7/2018 | Tatalovich et al. |
| 10,070,878 B2 | 9/2018 | Ma |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,258,452 B2 | 4/2019 | Eckhouse et al. |
| 10,265,086 B2 | 4/2019 | Vale et al. |
| 10,271,864 B2 | 4/2019 | Greenhalgh et al. |
| 10,278,816 B2 | 5/2019 | Miller et al. |
| 10,335,186 B2 | 7/2019 | Rosenbluth et al. |
| 10,342,570 B2 | 7/2019 | Richter et al. |
| 10,420,581 B2 | 9/2019 | Hehrlein et al. |
| 10,441,745 B2 | 10/2019 | Yang et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,653,426 B2 | 5/2020 | Yang et al. |
| 10,653,434 B1 | 5/2020 | Yang et al. |
| 10,661,053 B2 | 5/2020 | Yang et al. |
| 10,695,159 B2 | 6/2020 | Hauser |
| 10,716,880 B2 | 7/2020 | Culbert et al. |
| 10,786,270 B2 | 9/2020 | Yang |
| 10,835,272 B2 | 11/2020 | Yang |
| 10,835,711 B2 | 11/2020 | Yang et al. |
| 10,856,898 B2 | 12/2020 | Matsushita et al. |
| 10,888,280 B2 | 1/2021 | Newberry |
| 11,020,030 B2 | 6/2021 | Tao et al. |
| 11,065,018 B2 | 7/2021 | Buck et al. |
| 2001/0031980 A1 | 10/2001 | Wensel et al. |
| 2001/0031981 A1 | 10/2001 | Evans |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg |
| 2002/0156460 A1 | 10/2002 | Ye |
| 2002/0169467 A1 | 11/2002 | Heitzmann |
| 2002/0177899 A1 | 11/2002 | Eum et al. |
| 2002/0188314 A1 | 12/2002 | Anderson et al. |
| 2003/0088266 A1 | 5/2003 | Bowlin |

(56) References Cited

U.S. PATENT DOCUMENTS

| | | |
|---|---|---|
| 2003/0135193 A1 | 7/2003 | Hilgers et al. |
| 2003/0135198 A1 | 7/2003 | Berhow et al. |
| 2003/0153874 A1 | 8/2003 | Tai |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri |
| 2004/0153049 A1 | 8/2004 | Hewitt et al. |
| 2004/0199201 A1 | 10/2004 | Kellett |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell |
| 2005/0103332 A1 | 5/2005 | Gingles et al. |
| 2005/0137680 A1 | 6/2005 | Ortiz et al. |
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0217664 A1 | 9/2006 | Hattler et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264865 A1 | 10/2009 | Kawai |
| 2009/0270888 A1 | 10/2009 | Patel |
| 2009/0275974 A1 | 11/2009 | Marchand et al. |
| 2009/0312699 A1 | 12/2009 | Pudelko |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0295217 A1 | 12/2011 | Tanaka et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0290067 A1 | 11/2012 | Cam et al. |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131641 A1 | 5/2013 | Jimenez et al. |
| 2013/0131710 A1 | 5/2013 | Carmeli |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisel et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0173782 A1 | 6/2015 | Garrison et al. |
| 2015/0174363 A1 | 6/2015 | Sutermeister et al. |
| 2015/0257659 A1 | 9/2015 | Broers et al. |
| 2015/0269825 A1 | 9/2015 | Tran |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2016/0000443 A1 | 1/2016 | Lilburn et al. |
| 2016/0008572 A1 | 1/2016 | Di Caprio |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney |
| 2016/0206216 A1 | 7/2016 | Kirenko |

(56) References Cited

U.S. PATENT DOCUMENTS

| | | |
|---|---|---|
| 2016/0206322 A1 | 7/2016 | Fitz et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1* | 6/2017 | Kleshinski ............... A61F 2/014 |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0246014 A1 | 8/2017 | Rapaport et al. |
| 2017/0252057 A1 | 9/2017 | Bonnette et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0340867 A1 | 11/2017 | Accisano |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0228502 A1 | 8/2018 | Shaffer |
| 2018/0242980 A1 | 8/2018 | Lubock |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0338770 A1 | 11/2018 | Mogi et al. |
| 2019/0029825 A1 | 1/2019 | Fitterer et al. |
| 2019/0105477 A1 | 4/2019 | Heilman |
| 2019/0105478 A1 | 4/2019 | Malek |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0290884 A1 | 9/2019 | Kanemasa et al. |
| 2019/0336142 A1 | 11/2019 | Torrie |
| 2019/0336727 A1 | 11/2019 | Yang |
| 2019/0366041 A1 | 12/2019 | Yang |
| 2020/0001046 A1 | 1/2020 | Yang |
| 2020/0008820 A1 | 1/2020 | Aboytes et al. |
| 2020/0009301 A1 | 1/2020 | Yee |
| 2020/0022712 A1 | 1/2020 | Deville et al. |
| 2020/0046937 A1 | 2/2020 | Nakagawa et al. |
| 2020/0170521 A1 | 6/2020 | Gupta et al. |
| 2020/0025845 A1 | 7/2020 | Yang et al. |
| 2020/0297362 A1 | 9/2020 | Deville et al. |
| 2020/0297972 A1 | 9/2020 | Yee |
| 2020/0306501 A1 | 10/2020 | Yee |
| 2020/0323535 A1 | 10/2020 | Yang |
| 2021/0068852 A1 | 3/2021 | Spence |
| 2021/0093336 A1 | 4/2021 | Roue |
| 2021/0106238 A1 | 4/2021 | Strasser |
| 2021/0128182 A1 | 5/2021 | Teigen et al. |
| 2021/0153744 A1 | 5/2021 | Pierro |
| 2021/0186537 A1 | 6/2021 | Buck et al. |
| 2021/0187244 A1 | 6/2021 | Buck et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0316121 A1 | 10/2021 | Buck et al. |
| 2021/0316127 A1 | 10/2021 | Buck et al. |

FOREIGN PATENT DOCUMENTS

| | | |
|---|---|---|
| EP | 0 330 843 | 12/1993 |
| EP | 0 309 471 | 8/1996 |
| EP | 1 349 486 | 3/2008 |
| EP | 2 069 528 | 3/2013 |
| EP | 2 928 360 | 1/2017 |
| EP | 3 539 486 | 9/2019 |
| GB | 2077132 | 12/1981 |
| JP | 2002-535049 | 10/2002 |
| JP | 2003-527925 | 9/2003 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 1995/009659 | 4/1995 |
| WO | WO 2000/000100 | 1/2000 |
| WO | WO 2009/054968 | 4/2009 |
| WO | WO 2009/132218 | 10/2009 |
| WO | WO 2014/151209 | 9/2014 |

(56) References Cited

FOREIGN PATENT DOCUMENTS

| WO | WO 2014/203336 | 12/2014 |
| WO | WO 2017/025775 | 2/2017 |
| WO | WO 2018/121363 | 7/2018 |
| WO | WO 2019/178165 | 9/2019 |

OTHER PUBLICATIONS

Invitation to Pay Additional Fees for International Application No. PCT/US20/65349 dated Feb. 24, 2021.
International Search Report and Written Opinion dated May 7, 2021 in Application No. PCT/US2020/065349.
Guidezilla Guide Extension Catheter, Boston Scientific 510k Submission, Feb. 20, 2017.
Merit Medical Systems Acquired Distal Access's SPINR Platform, Jul. 15, 2015, Digital Access, LLC; Merit Medical Systems, 5 pages.
Simon et al., *Exploring the efficacy of cyclic vs. static aspiration in a cerebral thrombectomy model: an initial proof of concept study*, J. NeuroIntervent Surg 2014, 6 pp. 677-683.
Simon et al., *Hydrodynamic comparison of the Penumbra system and commonly available syringes in forced-suction thrombectomy*, J. NeuroIntervent Surg 2014, 6, pp. 205-211.
Spiotta et al., Evolution of thrombectomy approaches and devices for acute stroke: a technical review, J. NeuroIntervent Surg 2015, 7, pp. 2-7.
U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 16/863,723, filed Apr. 30, 2020, Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable Distal Opening.
U.S. Appl. No. 15/443,841 (U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular Catheter.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 16/542,657 (U.S. Pat. No. 11,147,949), filed Aug. 16, 2019 (Oct. 19, 2021), Method of Making an Enhanced Flexibility Neurovascular Catheter.
U.S. Appl. No. 17/502,389, filed Oct. 15, 2021, Neurovascular Catheter With Enlargeable Distal End.
U.S. Appl. No. 15/444,038 (U.S. Pat. No. 10,183,147), filed Feb. 27, 2017 (Jan. 22, 2019), Neurovascular Catheter Extension Segment.
U.S. Appl. No. 16/833,585, filed Mar. 28, 2020, Enhanced Flexibility Neurovascular Catheter.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/503,886, filed Jul. 5, 2019, Vacuum Transfer Tool for Extendable Catheter.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263 (U.S. Pat. No. 11,123,090), filed May 1, 2019 (Sep. 21, 2021), Neurovascular Catheter Having a Traumatic Angled Tip.
U.S. Appl. No. 16/570,084, filed Sep. 13, 2019, Enhanced Flexibility Neurovascular Catheter With Tensile Support.
U.S. Appl. No. 16/683,718 (U.S. Pat. No. 10,653,434), filed Nov. 14, 2019 (May 19, 2020), Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port).
U.S. Appl. No. 17/410,162, filed Aug. 24, 2021, Neurovascular Catheter Having Angled Tip.
U.S. Appl. No. 16/589,563, filed Oct. 1, 2019, Devices and Methods for Removing Obstructive Material From an Intravascular Site.
U.S. Appl. No. 17/036,258, filed Sep. 29, 2020, Embolic Retrieval Catheter.
U.S. Appl. No. 17/070,832 (U.S. Pat. No. 11,134,859), filed Oct. 14, 2020 (Oct. 5, 2021), Systems and Methods for Multivariate Stroke Detection.
U.S. Appl. No. 17/407,852, filed Aug. 20, 2021, Systems and Methods for Multivariate Stroke Detection.
U.S. Appl. No. 16/728,469, filed Dec. 27, 2019, Neurovascular Access With Dynamic Assistance.
U.S. Appl. No. 17/125,723 (U.S. Pat. No. 11,065,018), filed Dec. 17, 2020 (Jul. 20, 2021), Methods and Systems for Advancing a Catheter to a Target Site.
U.S. Appl. No. 17/125,217, filed Dec. 17, 2020, Methods and Systems for Treating a Pulmonary Embolism.
U.S. Appl. No. 17/125,743, filed Dec. 17, 2020, Systems for Accessing a Central Pulmonary Artery.
U.S. Appl. No. 17/125,742, filed Dec. 17, 2020, Methods and Systems for Accessing and Retrieving Thrombo-Emboli.
U.S. Appl. No. 17/357,490, filed Jun. 24, 2021, Catheter System for Treating Thromboembolic Disease.
U.S. Appl. No. 17/357,558, filed Jun. 24, 2021, Aspiration System With Accelerated Response.
U.S. Appl. No. 17/357,643, filed Jun. 24, 2021, Hemostasis Valve.
U.S. Appl. No. 17/357,672, filed Jun. 24, 2021, Split Dilator Aspiration System.
U.S. Appl. No. 17/357,715, filed Jun. 24, 2021, Methods of Placing Large Bore Aspiration Catheters.
U.S. Appl. No. 17/475,202, filed Sep. 14, 2021, Enhanced Flexibility Neurovascular Catheter.
U.S. Appl. No. 17/343,004, filed Jun. 9, 2021, Catheter With Enhanced Tensile Strength.
U.S. Appl. No. 17/398,244, filed Aug. 10, 2021, Catheter With a Preset Curve.
U.S. Appl. No. 29/811,884, filed Oct. 18, 2021, Inline Fluid Filter.

* cited by examiner

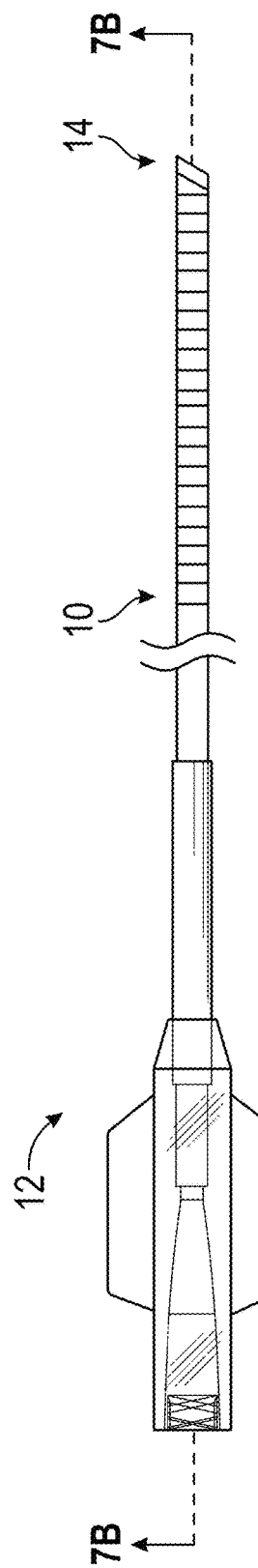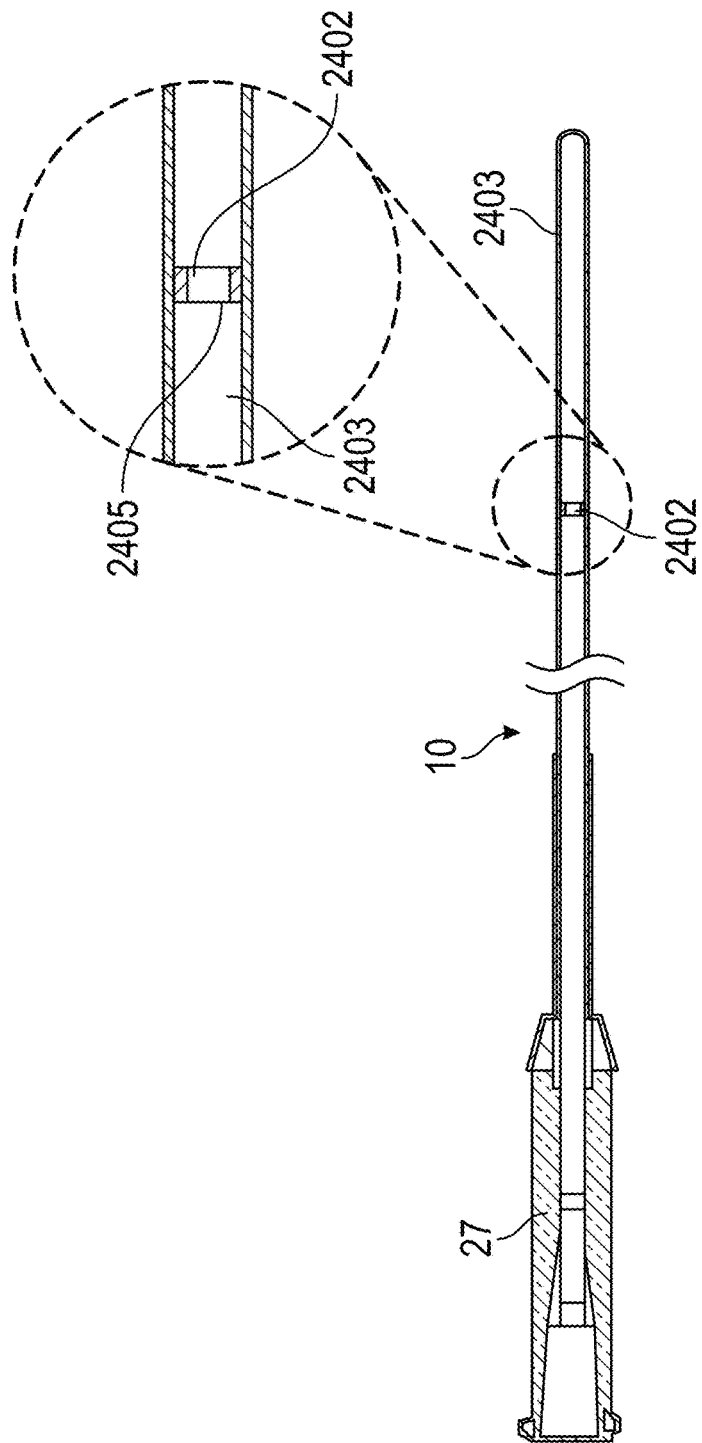

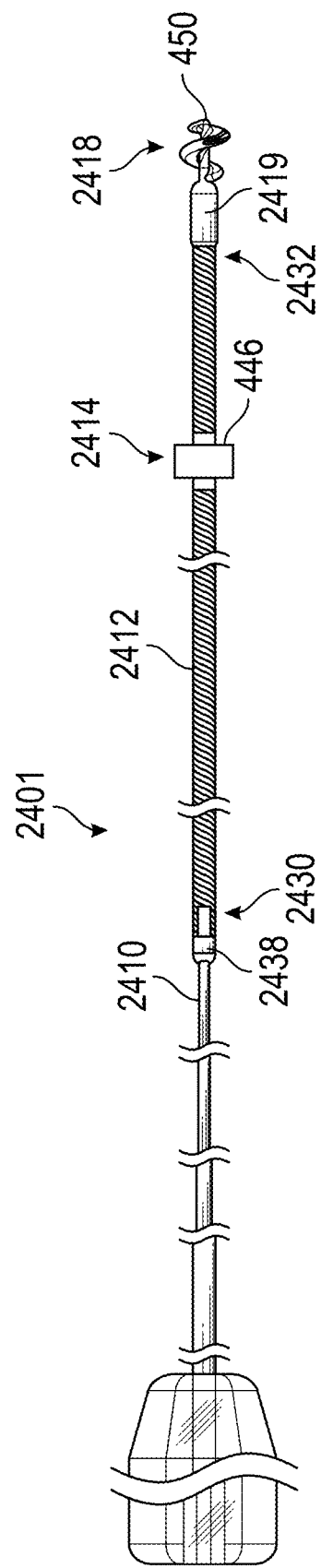

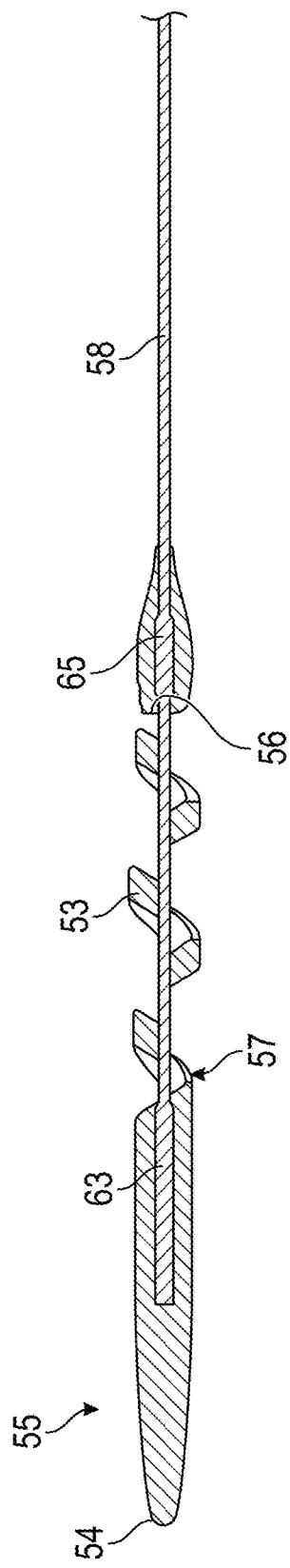
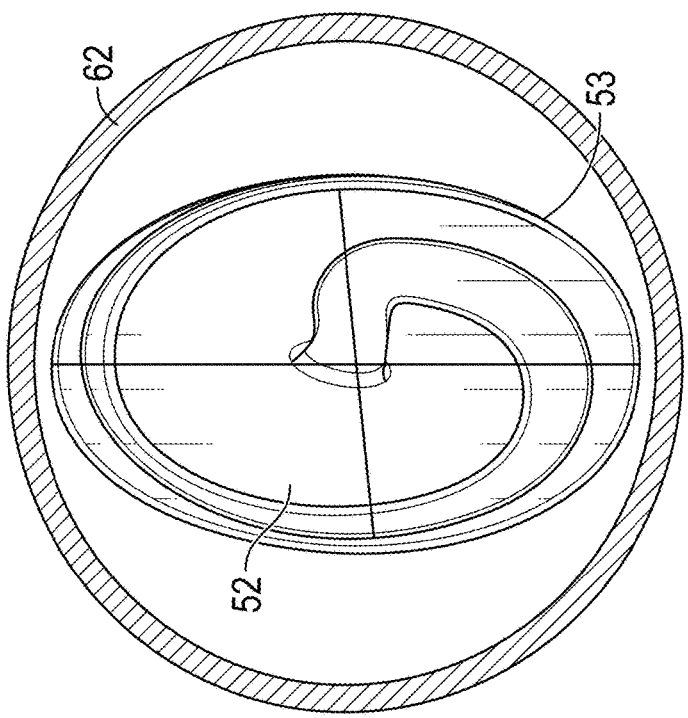

SYSTEMS FOR ACCESSING A CENTRAL PULMONARY ARTERY

CROSS-REFERENCE TO RELATED APPLICATIONS

This application claims the priority benefit under 35 U.S.C. § 119(e) of U.S. Provisional Patent Application No. 62/950,058, filed Dec. 18, 2019 and U.S. Provisional Patent Application No. 63/064,273, filed Aug. 11, 2020, the entirety of each of which is hereby incorporated by reference herein.

BACKGROUND OF THE INVENTION

Thrombotic restrictions and occlusions within a patient's blood vessels are a significant medical problem and often require intervention to remove these restrictions and blockages to restore health to patients. While applicable to a wide range of vascular applications, the following background illuminates the problems through the example of patients suffering with Pulmonary Embolisms.

Venous thromboembolic disease (VTE) is a worldwide crisis. There are over 10 million cases of deep vein thrombosis (DVT) and pulmonary embolism (PE) diagnosed globally per year, with 1 million cases occurring in the United States and over 700,000 in France, Italy, Germany, Spain, Sweden, and the United Kingdom combined each year. There are approximately 60,000 to 100,000 deaths from PE in the United States each year. DVT and PE are part of the same continuum of disease, with over 95% of emboli originating in the lower extremities. When PE occurs, the severity depends on the embolic burden and its effect on the right ventricle as well as underlying cardiopulmonary comorbidities. Death can result from the acute increase in pulmonary artery (PA) pressure with increased right ventricular (RV) afterload and dysfunction.

Patients with high-risk pulmonary embolism (PE) were treated primarily with thrombolytic therapy delivered systemically or more locally through Catheter Directed Thrombolytics. These approaches result in multiple catheterization lab visits, lengthy hospital stays and often lead to bleeding complications. Newer approaches to PE treatment include single session thrombectomy treatments without the use of thrombolytics. These thrombectomy treatments include delivering a catheter into the PA to remove the thrombus through aspiration, and secondary tools may also macerate or disrupt the thrombus prior to aspiration. While thrombectomy results in fewer bleeding complications and reduced hospital stays compared to thrombolytics, there is much to be improved upon given the challenges of the procedure itself, including the ability to capture a broad spectrum of thrombus types and reduce the total volume of blood loss during the procedure.

The thrombectomy catheter is introduced through an introducer puncture in a large diameter vein. A flexible guide wire is passed through the introducer into the vein and the introducer is removed. The flexible guidewire provides a rail for a flexible guide catheter to be advanced through the right atrium into the right ventricle and into the pulmonary artery. The flexible guidewire is removed and replaced with a stiff guidewire. The large diameter thrombectomy catheter with support dilator is then advanced over the stiff guidewire to the pulmonary artery and the dilator is removed. If the large diameter thrombectomy catheter is not successful in accessing or aspirating thrombus in a more distal portion of the vessel, a smaller diameter catheter may be inserted through the large diameter catheter. This procedure, with multiple accessory devices and exchanges, is expensive, requires advanced catheter skills, results in a high volume of blood loss, and may not result in optimal patient outcomes.

SUMMARY

There is provided in accordance with one aspect of the invention, a system for advancing a large bore catheter to a remote site, such as a central pulmonary artery. The system comprises an elongate, flexible tubular catheter, having a proximal end, a distal end and a catheter hub on the proximal end, and an elongate, flexible rail, having a proximal end, a distal advance segment having a distal end and a rail hub on the proximal end. The distal end of the rail extends at least about 5 cm or 10 cm or 15 cm or more beyond the distal end of the catheter when the catheter hub is adjacent the rail hub.

The system may further comprise an engagement structure on the catheter hub, configured to releasably engage a complementary engagement structure on the rail hub. The rail may increase in flexibility in a distal direction, and may include a guidewire lumen. The guidewire lumen may be configured to accommodate a guidewire having a diameter of no greater than about 0.035" and the rail has an outside diameter of no greater than about 0.025" smaller than the inside diameter of the aspiration catheter. The catheter hub may comprise a hemostasis valve.

The wall thickness of the rail may be at least about 0.05 inches, or at least about 0.10 inches. The rail may comprise a proximal segment separated from the distal advance segment by a transition. The distal advance segment may have a greater flexibility than the proximal segment.

The access catheter may be at least about 8 French, or at least about 20 French. The access catheter hub may comprise a projection configured to snap fit into a complementary recess on the rail hub.

The system may further comprise a thrombus evacuation catheter configured to extend through the access catheter, and may comprise a thrombus engagement tool configured to extend through the thrombus evacuation catheter. The thrombus engagement tool may comprise an elongate flexible body having a thrombus engagement tip with a helical thread. The thread may extend from about two to about 10 revolutions around the elongate flexible body. The thread may have a maximum diameter that is no more than about 60% of an inside diameter of an adjacent portion of the thrombus evacuation catheter. The thrombus engagement tool may further comprise a handle on the proximal end, configured to permit manual rotation of the thrombus engagement tool.

In accordance with another aspect of the invention there is provided a method of advancing a catheter to a target vascular site. The method comprises the steps of providing a catheter having a guiding rail extending therethrough, the catheter having a catheter distal end and the rail having a rail distal end. With the rail distal end positioned at least about 10 cm distal to the catheter distal end, advancing the rail distal end to the target vascular site; and thereafter advancing the catheter along the guiding rail to the target vascular site. The advancing the rail step may be accomplished by advancing the rail over a guidewire. The advancing the rail step may be accomplished while the rail distal end is at least about 10 cm distal to the catheter distal end. The method may further comprise the step of unlocking the catheter from the guiding rail prior to the advancing the catheter along the guiding rail step.

The advancing the rail distal end step may comprise advancing the rail distal end from the vena cava through the tricuspid and pulmonary valves of the heart into the central pulmonary artery while the distal end of the catheter remains in the vena cava. The advancing the catheter step may comprise advancing the catheter distal end from the vena cava through the tricuspid and pulmonary valves of the heart into the central pulmonary artery over the guiding rail, following locating the distal end of the rail in the central pulmonary artery.

The advancing the rail distal end step may comprise advancing the rail distal end from the vena cava through the tricuspid valve before advancing the catheter along the rail.

The advancing the catheter step may be accomplished over a guidewire, and may be accomplished with a guidewire extending through a cannulation in the rail, or may be accomplished with a guidewire extending through the catheter. The catheter may be at least about 8 French, or at least about 24 French, and the rail may substantially fill (e.g., at least about 80% or 90% or more of the cross section of) the catheter lumen.

The advancing the rail distal end step may comprise advancing the rail distal end through at least one valve before advancing the catheter along the rail and through the valve. The advancing the rail distal end step may comprises advancing the rail distal end through a vascular obstruction before advancing the catheter along the rail and through the obstruction. The advancing the rail distal end step may comprise advancing the rail distal end through a tissue aperture before advancing the catheter along the rail and through the aperture.

The method may further comprise the step of removing the rail following the advancing the catheter step, and may further comprise the step of advancing a clot evacuation catheter through the lumen to the target vascular site. The method may further comprise the step of applying vacuum to the clot evacuation catheter, and may further comprise the step of advancing a thrombus engagement tool through the clot evacuation catheter. The thrombus engagement tool may be manually rotated to engage the thrombus.

In accordance with a further aspect of the invention, there is provided a method of removing a clot from a pulmonary artery to treat a pulmonary embolism. The method comprises the steps of providing a large bore catheter having a guiding rail extending therethrough, the large bore catheter having a large bore catheter distal end and the rail having a rail distal end. With the rail distal end at least about 15 cm distal to the large bore catheter distal end, the rail distal end is advanced from the vena cava through the tricuspid and pulmonary valves of the heart into the central pulmonary artery while the distal end of the large bore catheter remains in the vena cava. The large bore catheter is thereafter advanced distally over the rail until the large bore catheter distal end is at least as far as the central pulmonary artery. The rail is thereafter proximally removed from the large bore catheter, and at least a portion of a clot is drawn from a pulmonary artery into the large bore catheter. The drawing step may be accomplished using vacuum.

The method may further comprise the step of advancing a clot capture catheter through the large bore catheter following the proximally removing the rail step, and may further comprise the step of advancing a clot engagement tool through the clot capture catheter. The clot engagement tool may be manually rotated to engage the clot.

There is also provided a method of removing foreign material from the vascular system, comprising the steps of positioning the distal tip of a sensing catheter in proximity to a target foreign material; propagating a signal from the sensing catheter; receiving a return signal; and capturing and removing at least a portion of the foreign material when the return signal is indicative of a foreign material located within a capture zone. The capturing and removing steps may be accomplished by the sensing catheter. The method may further comprise removing the sensing catheter following the receiving a return signal step, and introducing a clot capture catheter to accomplish the capturing and removing steps.

The foreign material may be a clot, which may be in the venous system, such as a deep vein thrombosis or a pulmonary embolism.

The return signal may enable characterization of tissue within the capture zone, and may enable differentiation between clot and vessel wall within the capture zone. The propagating a signal step may comprise propagating an ultrasound signal or an electromagnetic signal such as in the UV-visible range. The electromagnetic signal may comprise multiple wavelengths.

The propagating a signal step may comprise propagating visible light through the sensing catheter and beyond the distal tip. The method may further comprise receiving the return signal using a sensor carried by the sensing catheter. A visible light pathway may be created through blood between the distal tip and the target foreign material. The step of creating a visible light pathway through blood between the distal tip and the target foreign material may comprise infusing an optically transparent medium to displace blood from the pathway. The method may further comprise the step of deploying a barrier to temporarily contain at least a portion of the optically transparent medium within the pathway. The barrier may be deployed from the sensing catheter or from the aspiration catheter.

The differentiation may be accomplished by a clinician, observing an image generated by the return signal. The differentiation may be accomplished by a processor configured to differentiate between return signals indicative of either a foreign material or a vessel wall. The processor may further be configured to generate an indicium in response to the differentiation between a foreign material and a vessel wall. The indicium may comprise an audio or visual signal. The sensing catheter may be axially reciprocally introduced through an access catheter. The method may further comprise the step of proximally retracting the sensing catheter through the access catheter following the receiving a return signal, and may further comprise the step of distally advancing a clot capture catheter through the access catheter and capturing and removing at least a portion of the foreign material using the clot capture catheter.

Any of the methods disclosed herein may further comprise the step of deflecting the tip laterally in response to detecting vessel wall within the capture zone, prior to the capturing and removing steps.

In accordance with a further aspect of the invention, there is provided a dual dilator access system, comprising a large diameter access catheter, having an elongate tubular body with a proximal end, a distal end and a central lumen extending axially therethrough. A small diameter catheter is axially movably slidable through the central lumen. A first dilator is extendable through the central lumen, in between the small diameter catheter and the large diameter catheter; and a second dilator extendable through the small diameter catheter. The large diameter catheter may be an aspiration catheter. The small diameter catheter may be a clot grabber catheter.

The system may further comprise a proximal coupling for interlocking the large diameter catheter and the small diameter catheter. The first dilator may have a tapered distal end.

The large diameter access catheter may be at least about 14 French. The tapered distal end may be positionable beyond the distal end of the small diameter catheter. The clot grabber catheter may include a distal tip with a helical thread. The small diameter catheter may comprises an imaging catheter.

The first dilator may have a split line along which it can split for proximal retraction and removal. The split line may comprise a weakening in the wall or an axial scoring line.

The large diameter access catheter may comprise an inside surface defining the central lumen, and the inside surface comprises at least one surface discontinuity for influencing the behavior of material drawn into the central lumen. The surface discontinuity may comprise a ridge. A plurality of axially extending, circumferentially spaced apart ridges may be provided along at least a distal zone of the catheter. The distal zone may extend proximally from the distal end within the range of from about 1 to about 20 cm, and the discontinuity may extend all the way to the proximal end of the catheter. The ridge may be in a spiral configuration. The surface discontinuity may comprise at least one ramp and edge for permitting material to travel proximally in the central lumen and resisting distal travel of the material in the lumen. There may be a plurality of ramps which incline radially inwardly in the proximal direction and each terminate in a proximal edge. The central lumen may have a non circular transverse cross sectional configuration.

BRIEF DESCRIPTION OF THE DRAWINGS

FIG. 7A is a side elevational view of a catheter having an internal stop ring.

FIG. 7B is a longitudinal cross section through the catheter of FIG. 8A, and detail view of the stop ring.

FIG. 7C is a side elevational view of a thrombus engagement tool having a complementary limit for engaging the stop ring of FIGS. 7A and 7B.

FIGS. 8A-8C are side elevational and cross sectional views of tip profiles, showing proximal and distal tapers of the helical thread envelope.

FIG. 9 is an end elevational view of a helical tip having circumferentially varying major diameter creating a radially non-uniform separation from the catheter lumen wall.

DETAILED DESCRIPTION OF THE PREFERRED EMBODIMENT

Figure 1A:
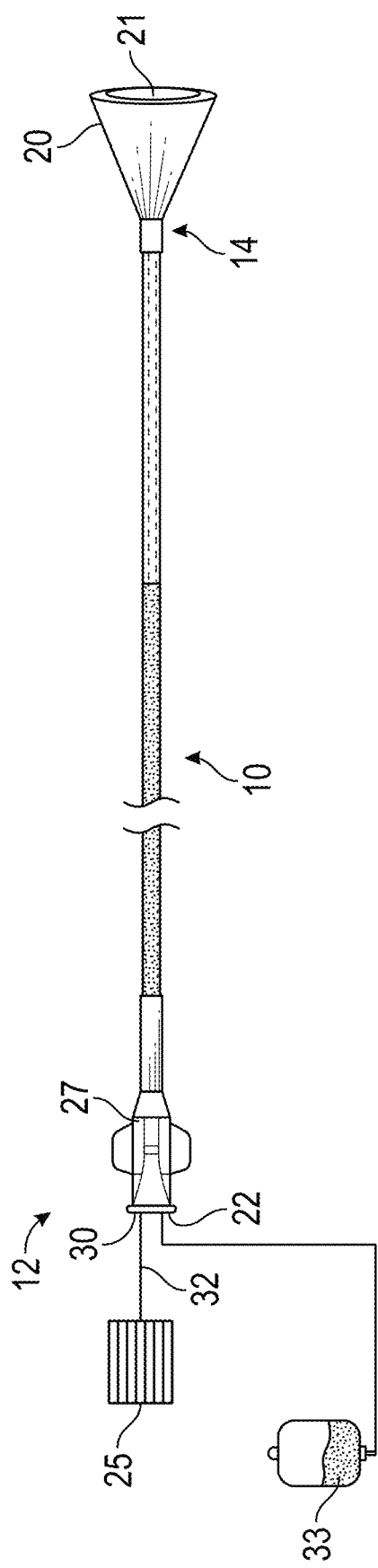
FIG. 1A is a schematic side elevational view of a thromboembolic imaging catheter.

The devices and systems of the present invention include catheter-based technology that enables accessing and retrieving a vascular obstruction. In some implementations of the system, a separate facilitator maybe provided for advancing through an aspiration catheter to facilitate engagement of the obstruction. In other implementations of the system, sensors are provided which provide the clinician with information about the presence, amount, and characteristics of tissue in front of the catheter. This enables valuable diagnostic information such as the identity of tissue within a clot capture zone adjacent and beyond the distal tip of the catheter, e.g., whether the catheter is aimed at clot or at the vessel wall, and potentially assists in developing an appropriate treatment strategy. As used herein, terms like clot, thrombus, embolization, foreign matter and the like will be considered synonymous unless otherwise described.

For instance, when planning to remove a pulmonary embolism from a pulmonary artery, it may be valuable to differentiate thrombus from vascular tissue and confirm 1) the presence and location of the thrombus, 2) the size and shape of the thrombus, and 3) the morphology and composition of the thrombus. All of these can be accomplished utilizing the single, low profile catheter in accordance with the present invention. The present sensing catheter described in further detail below includes, but is not limited to one or more sensors of the following modalities: CMOS imaging (or CCD) to enable visualization; thermal sensing; force sensing; ultrasound imaging; infrared imaging; spectroscopy tomography; or electrochemical sensing.

The sensing catheter is thus enabled to provide clinical data of the following types: Location of target obstruction; thrombus versus tissue wall; size and shape; mechanical properties like hardness/stiffness; temperature differences; or morphology/age.

Although primarily described in the context of a pulmonary artery embolectomy catheter with a target tissue characterization feature, catheters of the present invention can readily be adapted for use in removal of deep vein thrombosis or other vascular (e.g., neurovascular, other peripheral vascular, coronary), emboli or obstructions as will be understood in the art. Any of the devices disclosed herein can also be modified to incorporate additional structures, such as clot grabbing and retrieval features, partial length or full length guidewire lumen for over the wire or rapid exchange guidance, permanent or removable column strength enhancing mandrels, two or more lumens such as to permit drug, contrast or irrigant or optical field clearing infusion or to supply inflation media to an inflatable balloon carried by the catheter.

Any of the catheters disclosed herein may have a deflectable or preshaped curved or angled distal steering zone. At least one and optionally two or three or more pull wires may axially extend through corresponding pull wire lumen(s), to enable lateral deflection of the distal tip of the catheter. A single pull wire can provide deflection in a single direction and plane, to cooperate with rotation of the catheter to achieve 360 degree maneuverability. Two or three or more pull wires, typically spaced equidistantly around the circumference of the catheter body, enable greater steerability without the need for catheter rotation. Deflection or preshaped curvature or angulation of the distal tip enables redirection of the tissue capture zone away from a first target tissue (e.g., healthy vessel wall) to a second target tissue (e.g., a clot). Catheters of the present invention can include any combination of the foregoing features, depending upon the intended clinical application and desired functionality as will be readily apparent to one of skill in the art in view of the disclosure herein.

In addition, the present invention will be described primarily in the context of removing obstructive material from the pulmonary artery but may have applicability for use throughout the body wherever it may be desirable to characterize a target tissue to support a clinical decision to remove or treat a first target tissue or redirect the catheter to a different, second target tissue. For example, sensing catheter shafts in accordance with the present invention may be dimensioned for use throughout the coronary, peripheral, and neurovasculature, both arterial and venous, the gastrointestinal tract, the urethra, ureters, Fallopian tubes and other lumens and potential lumens, as well. The sensing catheter of the present invention may also be used to provide minimally invasive percutaneous tissue access, such as for diagnostic or therapeutic access to a solid tissue target (e.g., breast or liver or brain biopsy or tissue excision), access to bones such as the spine for surface characterization and other applications.

Figure 1C:
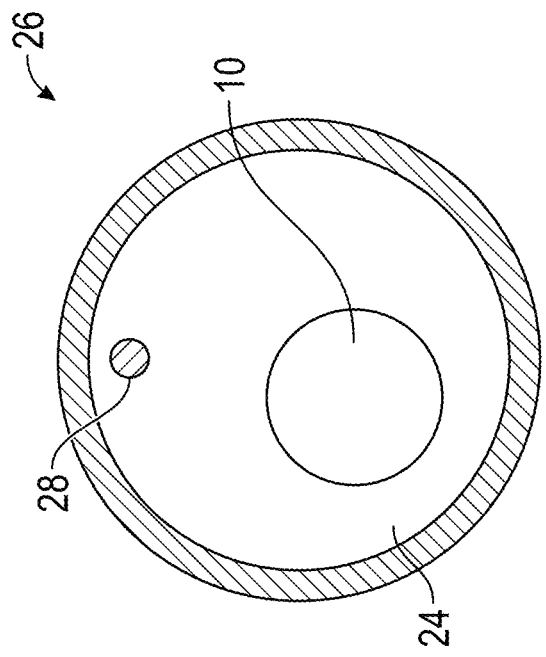
FIG. 1C illustrates the catheter of FIG. 1A, extending through a lumen in an aspiration catheter.
Figure 1B:
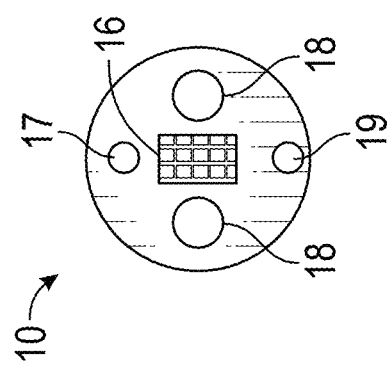
FIG. 1B is a distal end view of the catheter of FIG. 1A.

Referring to FIGS. 1A and 1B, a sensing catheter generally comprises an elongated flexible tubular body 10 extending between a proximal end 12 and a distal functional end 14. The length of the tubular body depends upon the desired application. For example, catheter lengths from about 120 cm to about 150 cm or more are typical for use in femoral access percutaneous transluminal coronary applications. Intracranial or other applications may call for a different catheter shaft length depending upon the vascular access site, as will be understood in the art.

In certain embodiments intended to treat pulmonary embolism via a femoral vein access site, the catheter 10 will generally have an axial length within the range of from about 80 cm to about 110 cm for a primary treatment catheter and from about 130 cm to about 150 cm for a secondary catheter intended to advance through a primary catheter. Outside diameters may be within the range of from about 8 F to about 32 F depending upon the procedure and intended clinical performance.

The distal end 14 of catheter 10 is provided with at least one sensor 16 for characterizing the clot, vessel wall, or other target tissue. In an embodiment intended for optical visualization, an optical sensor such as a CMOS or CCD chip may be located at the distal end of the catheter, or in a proximal handpiece or module, and optically coupled to a fiber optic element extending axially throughout the length of the catheter. A light source such as an LED is also provided, either at the distal end of the catheter, or at the proximal end of the catheter and optically coupled to a fiber optic light guide extending through the catheter body.

The catheter 10 may additionally be provided with a guide wire lumen 17 extending between a guide wire port on the distal end 14 of the catheter 10 and a proximal guide wire port. The proximal guide wire port may be through a sidewall of the catheter 10 in a rapid exchange implementation, or may be provided on the hub 27 in an over the wire configuration. One or two or more additional ports or electrical connectors may be provided on the proximal hub 27, depending upon the functionality of the catheter.

The catheter is provided with at least one infusion lumen 18, and two in the illustrated embodiment, extending from a proximal infusion port 22 on a proximal hub 27 to a corresponding exit port on the distal end 14 of the catheter. A deflection mechanism may be provided, for laterally deflecting a distal steering zone on the catheter 10. In one implementation, a pull wire lumen 19 extends from a proximal deflection control (not illustrated) carried by the hub 27 and extending distally to the deflection mechanism. The proximal control may comprise a rotatable control such as a ring that may be rotatable about the longitudinal axis of the catheter, or a rotatable knob, a slider switch, or other suitable control for placing a control wire under tension or compression. The deflection mechanism may form a deflection zone on a distal portion of the catheter 10, in which an axial length of the catheter sidewall is provided on a first side with a plurality of transverse slots, leaving an opposing spine side with relatively higher column strength. The deflection wire may be attached to the side wall distally of the slots. Proximal retraction of the deflection wire causes axial compression of the slotted side of the tubular body thereby deflecting the axis away from the spine side and towards the slotted side of the tubular body.

In use, a fluid media, optically transparent in the visible range (e.g., water or saline) is infused from a source 33 and through lumen 18 to displace blood in a visualization and capture zone 21 in front of the catheter and create an optical path between the sensor and target tissue. A temporary barrier such as a hood 20 may be desirable to lengthen the dwell time of the optically transmissive media within the optical path, before it is replaced with blood and become optically opaque in the visual range.

In the illustrated embodiment, the barrier is in the form of an imaging hood 20 such as a self expandable cone, to protect the viewing area from blood flow. The barrier is carried by the distal end of the sensing catheter and may be self expanding upon release from a restraint such as the outer access catheter which may also be an aspiration catheter.

Alternatively, referring to FIG. 1C, the imaging hood 20 or other barrier may be carried by the aspiration catheter 26. In this implementation, the sensing catheter 10 may be advanced distally through a lumen 24 in the aspiration catheter 22, and the imaging hood 20 utilized as described to facilitate establishment of an optical path between the sensor and target tissue. The ID of the lumen 24 may be at least about 0.005" and in some implementations at least about 0.010" or 0.015" or more greater than the OD of the imaging catheter 10 to provide an aspiration lumen while the imaging catheter 10 is in place, and also accommodate a guidewire 28.

Following confirmation by the sensing catheter 10 that the aspiration catheter 26 is positioned at the desired site, the sensing catheter 10 may be proximally retracted and the central lumen 24 can be used for direct aspiration or to receive a clot capture catheter (discussed below) therethrough. At this point, the imaging hood 20 can perform the additional and distinct function of helping advance the clot proximally into the aspiration catheter.

Image data from the image sensor is carried proximally through the catheter by one or more conductors, to a connector 30, and via cable 32 into a processor 25 for converting into a visual image or other visual and/or audible indicium of characterization of the target tissue. The image can be displayed on a conventional display such as a laptop, tablet, wall hung display or wearable display.

Figure 2A:
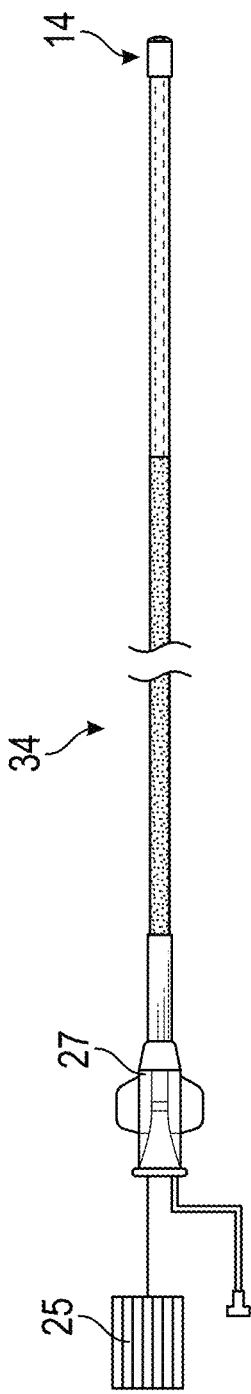
FIG. 2A is a schematic side elevational view of a thromboembolic thermal sensing catheter.
Figure 2B:
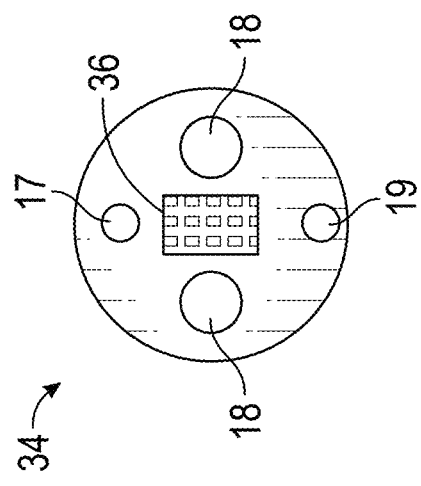
FIG. 2B is a distal end view of the catheter of FIG. 2A.

As an alternative to direct visualization in the visible light range, a variety of other characterizing modalities may be used to characterize target tissue. For example, referring to FIGS. 2A-2B, in a given environment, the foreign material and healthy wall may have different surface temperatures. In this situation, a thermal sensing catheter 34 may be provided with one or two or more distal temperature sensors 36. Intravascular thermal sensors are described, for example, in U.S. Pat. No. 9,420,955 entitled "Intravascular temperature Monitoring System and Method", the disclosure of which is hereby incorporated by reference in its entirety herein.

Alternatively, hemoglobin reflectivity measurement and optional simultaneous optical coherence tomography imaging capabilities may be added to the catheter, as described in US published patent application No. 2011/0077528 to Kemp et al, entitled Method and Apparatus for Simultaneous Hemoglobin Reflectivity Measurement and OCT Measurement, Thrombus Detection and Treatment, and OCT Flushing, published Mar. 31, 2011, which is hereby incorporated in its entirety herein by reference. Hemoglobin reflectivity measurement enables differentiation between 'red' thrombus and 'white' thrombus, which differ largely in the concentration of red blood cells.

Alternatively, a chemistry-based sensor may be used which uses the chemical composition of the tissue to create a signal which can differentiate between the foreign body and non-target tissue, or characterize different tissue types. For example, Fibrinogen has been reported to have been detected using an electrochemical impedance biosensor (EIB) formed by draping an erythrocyte membrane (EM) configured for the detection of fibrinogen. Measurements with the EIB may reveal that the specific (selective) adsorption of fibrinogen onto the EM causes a clear rise in the value of interfacial charge transfer resistance. The sensing ability of the EIB for fibrinogen detection may show a wide linear range from 0.0001 to 5 mg/mL, with a limit of detection of 49 ng/mL (144 pM).

Preferably the sensors in general detect a relatively high level of hemoglobin, or fibrinogen, or prothrombin, or other clotting pathway factors which would not be as abundant in vascular wall tissues.

Figure 3A:
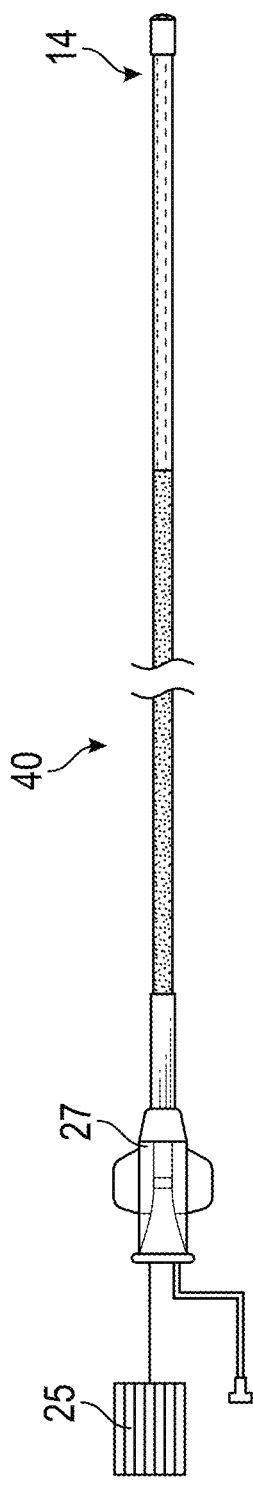
FIG. 3A is a schematic side elevational view of a thromboembolic force sensing catheter.
Figure 3B:
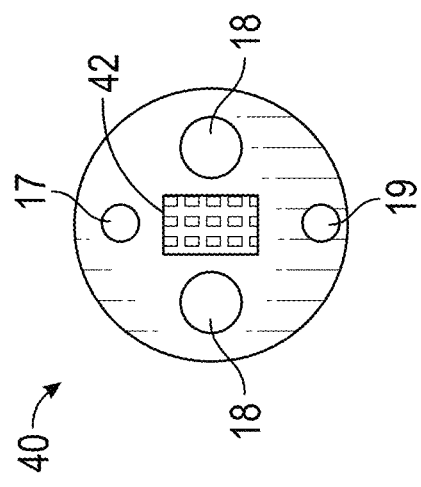
FIG. 3B is a distal end view of the catheter of FIG. 3A.

The clot and native vessel wall may also vary in physical properties such as compressibility or hardness. Referring to FIGS. 3A-3B, this may be measured by one or two or more force, pressure, or displacement sensors 28 carried by the distal end 14 of a force sensing catheter 40.

Figure 4A:
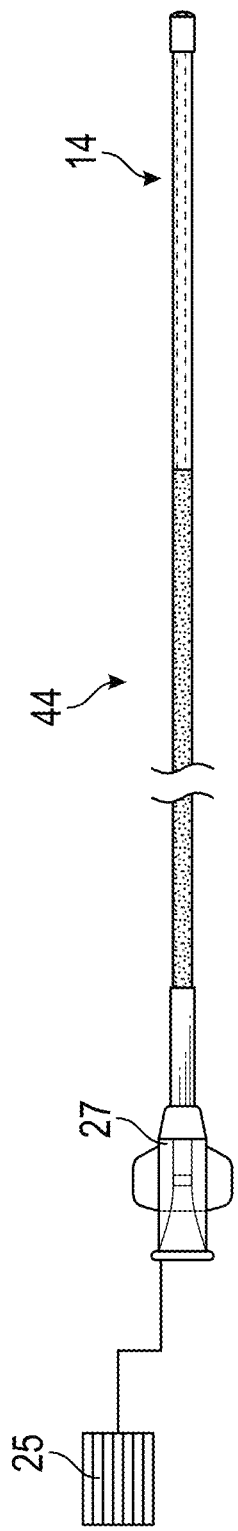
FIG. 4A is a schematic side elevational view of a thromboembolic ultrasound catheter.
Figure 4B:
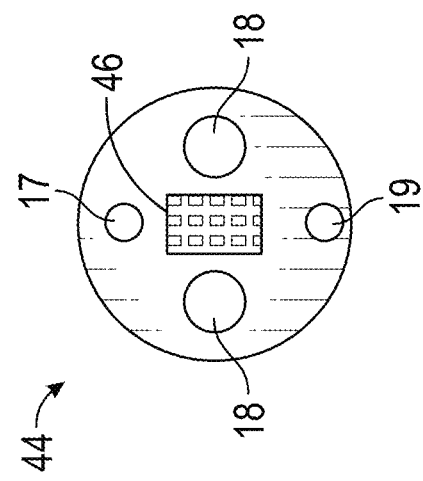
FIG. 4B is a distal end view of the catheter of FIG. 4A.

In certain embodiments it may be desirable to interrogate tissue within the capture zone with a first signal, and then capture reflected or rebounded signal for comparison to characterize the target tissue. For example, referring to FIGS. 4A-4B, ultrasound catheter 44 may be provided with ultrasound transmitter and receiver chips 46 which may be carried by the catheter 44 to interrogate tissue in the capture zone.

Figure 5A:
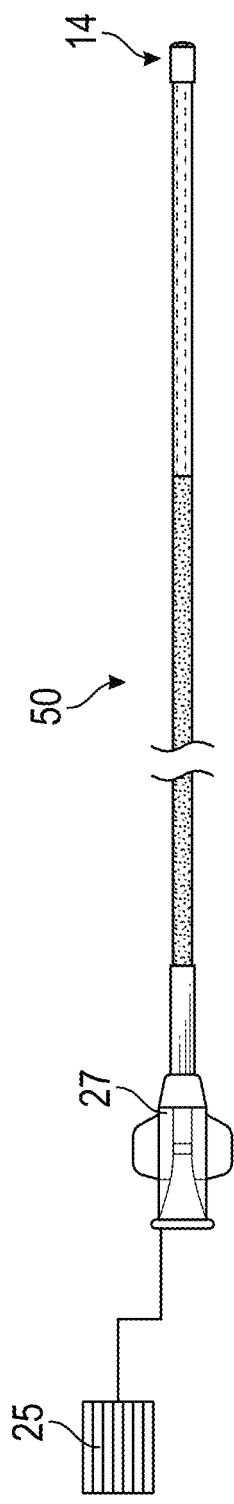
FIG. 5A is a schematic side elevational view of a thromboembolic electromagnetic spectrum imaging catheter.

Depending upon the nature of the target tissue and adjacent healthy tissue, any of a variety of other signals in the electromagnetic spectrum may be propagated from an EMS imaging catheter 50 with reflected signal captured by the catheter to identify and define matter in front of catheter. See, e.g. FIGS. 5A-5C.

EMS imaging catheter 50 may comprise one or two or more transmitters 52 for transmitting EMS imaging signals to target tissue and one or two or more receivers 53 for sensing reflected EMS signals. Aspiration lumen 54 may be provided, if aspiration is desired. One or more working channels or delivery channels 56 may be provided, depending upon the desired functionality.

Figure 5C:
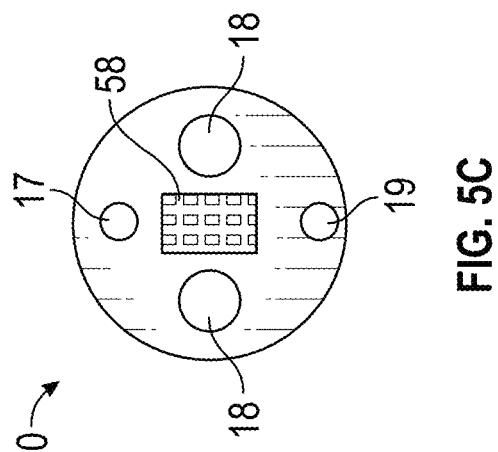
FIG. 5C is a distal end view of a variation of the catheter of FIG. 5A.
Figure 5B:
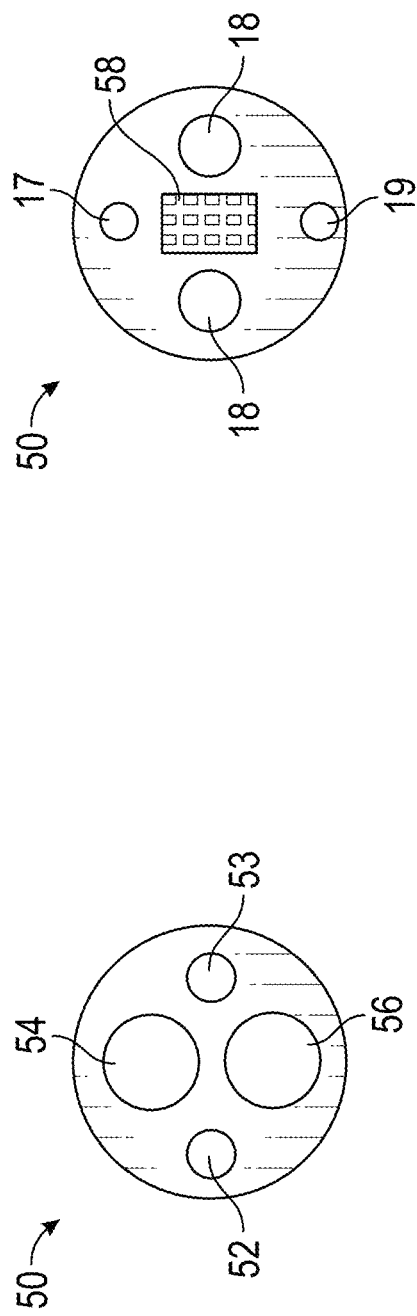
FIG. 5B is a distal end view of the catheter of FIG. 5A.

The number and orientation of lumen, electrical conductors and other structures within the catheter body can be varied widely depending upon the desired functionality of the catheter. For example, FIG. 5C illustrates an alternate configuration for the catheter of FIG. 5A, in which a guide wire lumen 17 has been provided along with a pull wire lumen 19 in a steerable implementation. An EMS sensor or sensor/receiver array 58 may be provided, along with one or two fluid lumen 18 such as for the delivery of saline and/or drug delivery and/or aspiration.

Intravascular sensing systems that may be adapted into the catheters of the present invention for characterizing material within the capture zone 21 as native vascular wall or foreign material are disclosed, for example, in U.S. Pat. No. 10,534,129, issued Jan. 14, 2020 and entitled "System and method providing intracoronary laser speckle imaging for the detection of vulnerable plaque"; U.S. Pat. No. 7,473,230, issued Jan. 6, 2009 and entitled "Instrumented catheter with distance compensation to sense vulnerable plaque"; and U.S. Pat. No. 7,450,241, issued Nov. 11, 2008 and entitles "Detecting vulnerable plaque", the disclosures of which are hereby incorporated in their entireties herein by reference.

In general, the distal end 14 of the sensing catheter 10 may be provided with at least one signal transmitting surface and at least one signal receiving surface. The transmitting surface is adapted to transmit a signal from the distal end of the catheter and generally in the distal direction with respect to the longitudinal axis of the catheter. The receiving surface is adapted for receiving a reflected return signal with at least a component of the signal traveling in a generally proximal direction with respect to the distal end of the catheter. In one embodiment, the transmitting surface comprises the distal end of a fiber optic or fiber optic bundle, a distal light source, or a transparent window which may be a lens positioned at the distal end of a fiber optic or fiber optic bundle or distal light source. Similarly, the receiving surface may comprise a distal end of a receiving fiber optic or a distal sensor, a transparent window which may be a lens positioned distally of the receiving fiber optic or sensor. In one embodiment, two transmitting surfaces and two receiving surfaces may be provided each communicating with a spectrometer via unique communication lines.

Electrical signals from the sensors may be transmitted to a spectrometer or other device suitable for the sensed signal, which remains outside of the patient. The construction and use of spectrometers such as to measure RGB and other UV, visible and IR wavelengths is well understood in the pulse oximetry art, among others, and will not be disclosed in detail herein. In general, a transmitter/detector may be able to transmit multiple wavelengths of light, which propagate beyond the transmit surface and into a target beyond the distal end of the sensing catheter. Some of the transmitted light is absorbed in the target, while other transmitted light is reflected back and received at the receiving surface. The reflected light is thereafter propagated for processing. The optical absorption/reflection characteristics of the clot compared to healthy vessel wall enable differentiation of the target tissue types.

Any of the foregoing sensing catheters may be utilized in the image-guided PE or DVT thrombectomy system and procedure in accordance with the present invention.

Figure 6:
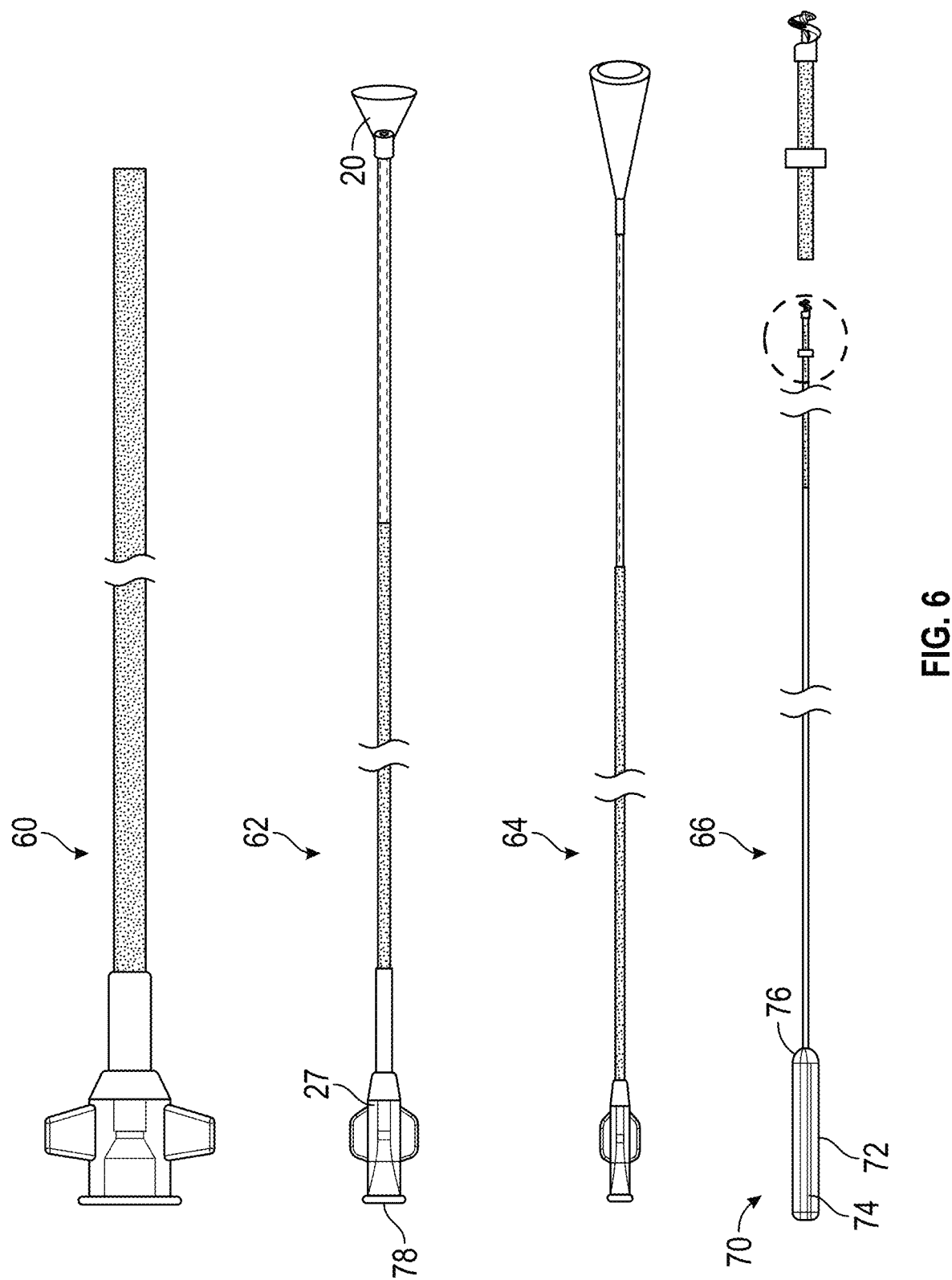
FIG. 6 is a side elevational view of the components in a thromboembolic visualization and aspiration system.

Referring to FIG. 6, the system for accessing and retrieving thrombo-emboli in accordance with the present invention generally comprises an access catheter 40 such as a large bore (e.g. 24 Fr) catheter, an aspiration or evacuation catheter 62, optionally an imaging functionality, which may be a separate sensing catheter 64, and a clot retrieval tool 66 configured to be extendable through the evacuation catheter 62.

One example of the method and use of the system is described below.

Femoral vein or internal jugular vein access is achieved using conventional techniques.

An access catheter 60 such as a 24 Fr catheter is advanced through the right heart chambers and into the Pulmonary Artery.

Aspiration may be applied to the access catheter for clot removal in the proximal pulmonary artery. If that fails, a mechanical facilitator device such as clot retrieval tool 66 may be advanced through the access catheter 60 to assist with clot removal. If that fails, the evacuation catheter 62 may be advanced through the 24 Fr access catheter 40 and advanced to the thrombus.

If desired, the imaging catheter 64 may be advanced through the evacuation catheter 62 to identify and verify thrombus. Alternatively, when the imaging and evacuation catheters have been integrated, only one catheter with both imaging elements and an evacuation lumen would need to be advanced through the 24 Fr access catheter 40 at this stage.

Aspiration is turned on to hold thrombus in place at the evacuation collection funnel 20 while exchanging Imaging Catheter 64 for the clot retrieval catheter 62.

The thrombus engagement tool 66 may be advanced into the thrombus for thrombus engagement.

The thrombus engagement tool 66, evacuation catheter 62 and engaged thrombus are proximally retracted through the 24 Fr catheter 60. Retraction may be accomplished under optional aspiration to maintain attachment of the thrombus.

Optionally, the imaging catheter 64 may be reintroduced to confirm target thrombus removal and identify additional thrombus to remove.

Aspiration, exchange, engage, extract, re-image may be repeated as desired.

Following aspiration, all catheters may be removed.

Additional details of the devices useful in the methods and systems of the present invention are discussed below.

Referring to FIGS. 7A and 7B, any of the aspiration catheters disclosed herein may be provided with an axial restraint for cooperating with a complementary stopper on a thrombus engagement tool 2401 (FIG. 7C) to permit rotation of the thrombus engagement tool 2401 but limit the distal axial range of travel of the thrombus engagement tool 2401.

The method of limiting distal advance of the core wire and helical tip element may be achieved by a limit attached to the core wire or torque member in sliding contact with an internal stop as described above, or in sliding contact with a stop surface carried on any of a variety of accessories or devices attached to the proximal end of the catheter in which the helical member assembly is contained. This includes a Tuohy-Borst or other hemostasis valve accessory.

In the illustrated implementation, the restraint comprises at least one projection extending radially inwardly through the sidewall or from the inside surface of the tubular body, configured to restrict the inside diameter of the aspiration lumen and engage a distal face carried by the thrombus engagement tool. The restraint may comprise one or two or three or four or more projections such as tabs, or, as illustrated, may comprise an annular ring providing a continuous annular proximally facing restraint surface. In the illustrated implementation, the restraint is positioned in a distal location in the catheter e.g., within about 20 cm or 10 cm or less from the distal end. This allows precise positioning of the distal thrombus engagement tool tip with respect to the distal end of the catheter, decoupled from bending of the catheter shaft, and prevent the distal tip from extending beyond a preset position such as the distal end of the catheter.

In other implementations, the restraint may be located at the proximal end of the catheter such as at the proximal hub, or even external to the catheter, such as on the proximal end of the hub. For example, the thrombus engagement tool 66 may be provided with a handle 70 as illustrated in FIG. 6. Handle 70 comprise an axially elongate body 72 configured to be twirled about its longitudinal axis between two or three fingers of a single hand. Surface friction enhancing structures such as a plurality of axially extending flats or ridges 74 may be provided on an exterior surface of the body 72. Distal end 76 may be configured to rotatably slide against a proximal surface 78 on the hub 27 for evacuation catheter 62.

In certain clinical applications, it may be desirable for the helical tip to be able to advance beyond the tip of the surrounding catheter, thus an axial limit system may be omitted, or may be configured to permit the desired axial orientation. For example, distal extension of the distal end of the helical tip beyond the distal end of the catheter may be limited to no more than about 5 mm or 3 mm or 1.5 mm or 1.0 mm or less.

The limit on distal advance of the helical tip may include a first configuration in which distal advance is limited to a first position proximate the distal end of the evacuation catheter to prevent injury to the vascular wall. Upon a user initiated adjustment, the helical tip may be advanced to a second position out of the distal end of the catheter for inspection and cleaning purposes. This adjustment of the limiting mechanism may be locked out following cleaning or inspection, to limit distal travel to the first position to prevent an undesired degree of exposure of the helical tip element when the system is within the patient's vasculature.

In the illustrated embodiment, the restraint may be a metal (e.g., nitinol, stainless steel, aluminum, etc.) circular band or ring or protrusion 2402 mounted on or built into a sidewall 2403 of the catheter near the proximal hub, on the proximal hub on the proximal end of the catheter shaft or near the distal tip. The restriction element 2402 extends into the ID of the catheter. Further, the restriction element 2402 may be radiopaque for visibility under fluoroscopy. The restriction element 2402 carries a proximally facing surface 2405 for example an annular circumferential bearing surface that extends into the inner diameter of the catheter to provide a sliding interface with a stopper such as distal stopper 2414 (FIG. 7C) on the rotating core assembly. For example, the stopper 2414 may be a radially outwardly extending feature on the rotating assembly which interfaces with the restriction element 2402 of the catheter to permit rotation but limit the distal advancement and prevent distal tip displacement beyond a desired relationship with the catheter distal tip.

In one implementation, in its relaxed form prior to securing within the catheter lumen, the ring 2402 is a C-shaped or cylinder shaped with an axially extending slit to form a split ring. The ring 2402 is compressed using a fixture that collapses the ring to a closed circle shape, allowing it to slide inside the (e.g., 0.071″) catheter. When the ring is released from the fixture, the ring expands radially to the largest diameter permitted by the inside diameter of the catheter. The radial force of the ring engages the insider surface of the catheter and resists axial displacement under the intended use applied forces. In another implementation, the ring is a fully closed, continuous annular structure (like a typical marker band) and its distal end is slightly flared in a radially outwardly direction to create a locking edge. The ring is inserted into the catheter from the distal end. The flared section with the locking edge keeps the ring in place when axial force is applied from the proximal side.

Figure 7D:
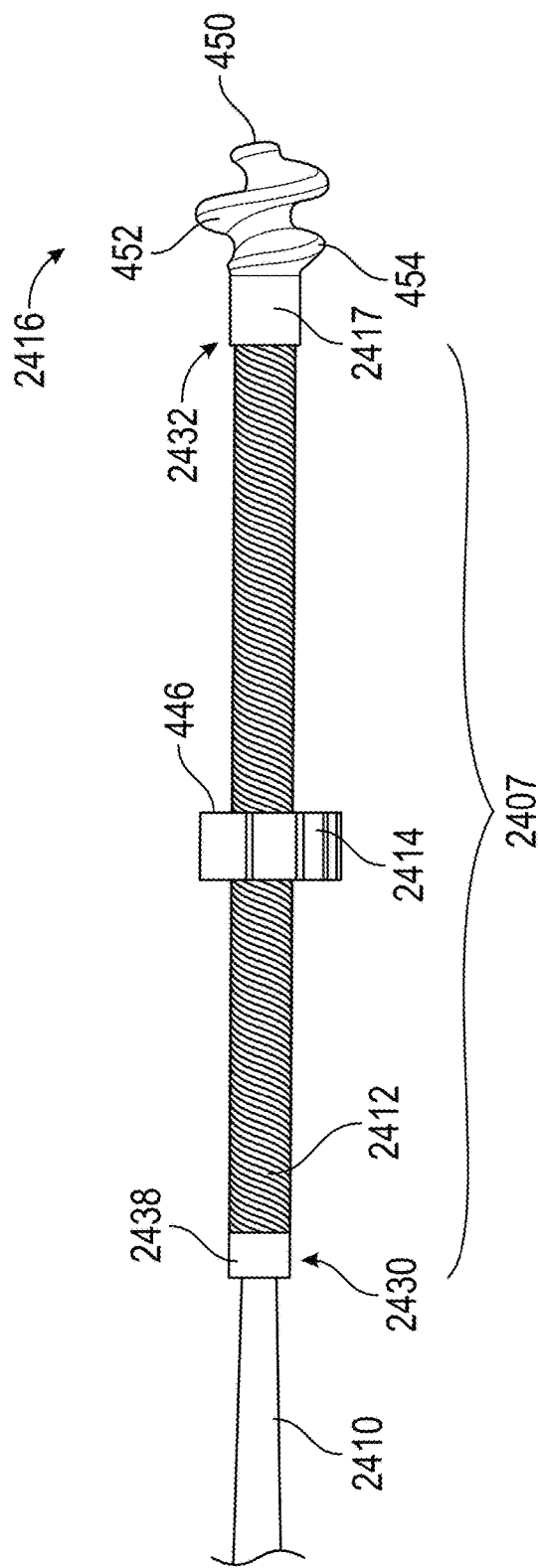
FIG. 7D is a side elevational view of a distal portion of the thrombus engagement tool of FIG. 7C.
Figure 7E:
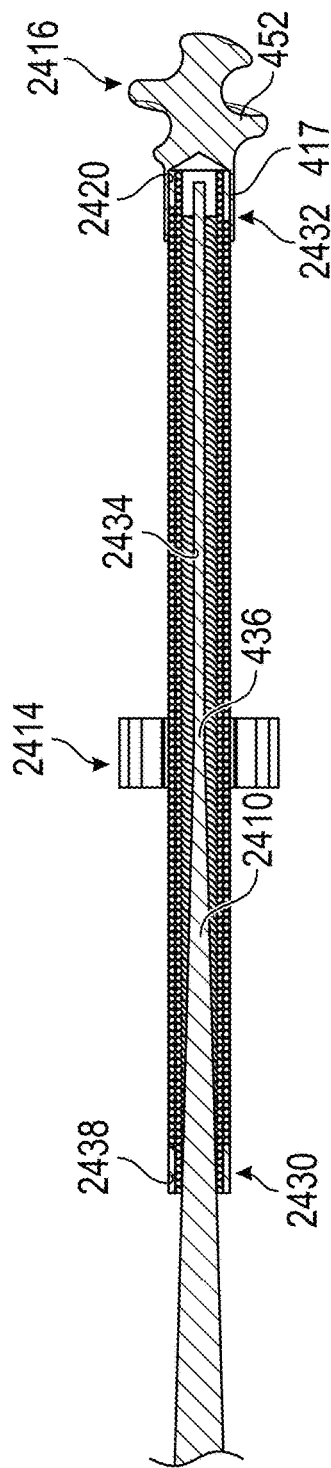
FIG. 7E is a longitudinal cross section through the thrombus engagement tool of FIG. 7D.
Figure 7F:
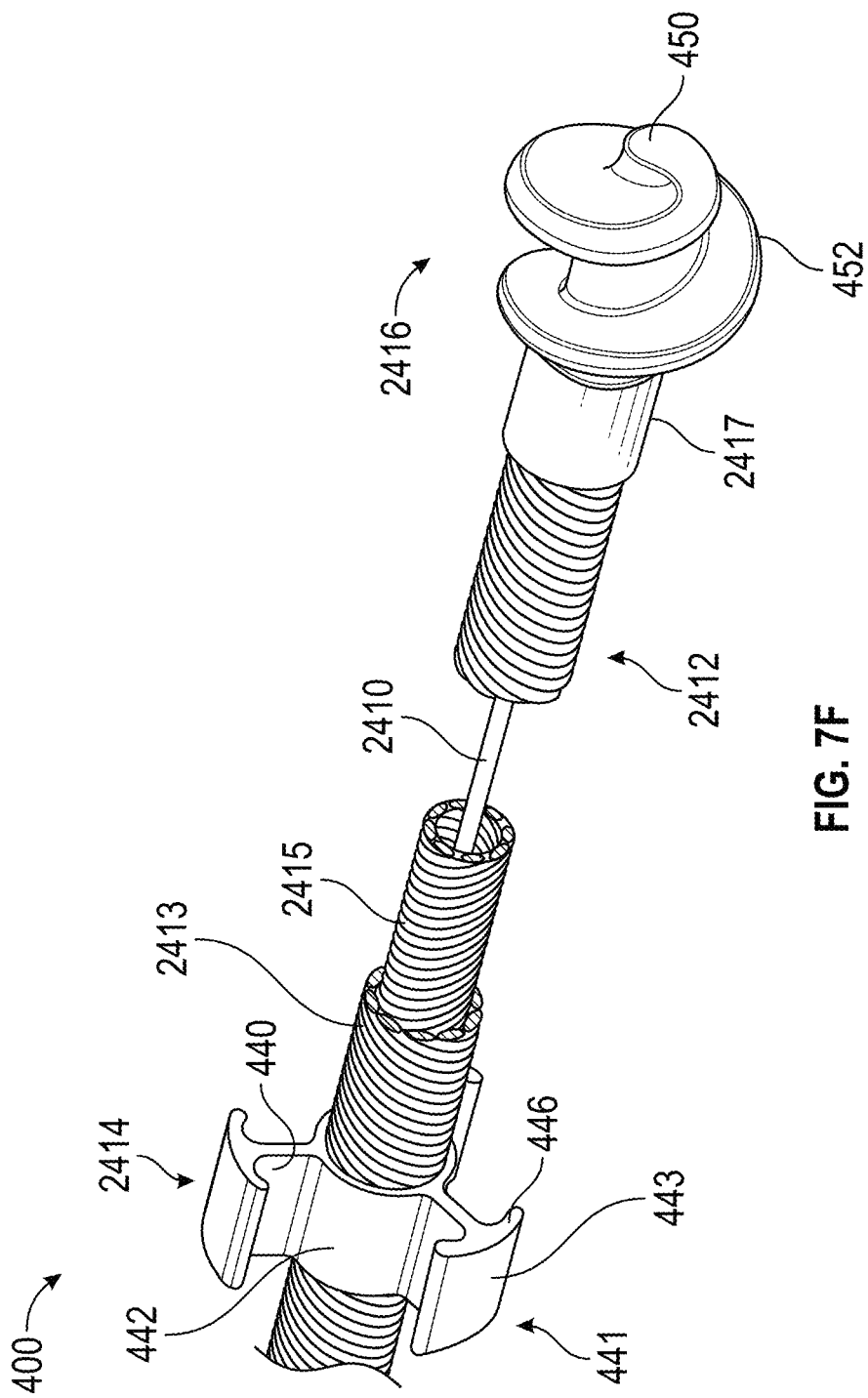
FIG. 7F is a perspective cut away view of a distal portion of the thrombus engagement tool of FIG. 7C.

Referring to FIGS. 7D and 7F, distal segment 2407 of the rotatable core wire comprises a torque coil 2412 surrounding a core wire 2410. The illustrated torque coil 2412 comprises an outer coil 2413 concentrically surrounding an inner coil 2415 having windings in opposite directions.

Alternatively, for an over-the-wire embodiment (e.g., FIG. 11) alternative torqueable structures may be utilized, including a polymeric tube with an embedded metallic wire braid intended to be entirely inserted over and rotated around a central guidewire. Additionally, the geometry of the lumen of the torqueing member may minimize the space between the lumen inner diameter and the guidewire so as to minimize fluid or airflow and virtually eliminate blood flow out of the lumen under biologically typical pressures or air leakage to significantly reduce vacuum pressures when a vacuum pump is used to create a vacuum through the aspiration catheter (60) near the distal end of the elongate structure.

Although the coil 2412 is shown in FIGS. 7D, 7E and 7F as having a constant diameter, this leaves an internal entrapped space between the coil and the core wire, as a result of the tapering core wire 2410. When the area of the aspiration lumen between the coil and the inside wall of the corresponding catheter is optimally maximized, the diameter of the coil 2412 can taper smaller in the distal direction to track the taper of the core wire. This may be accomplished by winding the coil onto the core wire which functions as a tapered mandrel, or using other techniques known in the art.

In this execution, the OD of the core wire tapers smaller in the distal direction, while the area of the aspiration lumen tapers larger in the distal direction.

As illustrated further in FIGS. 7D and 7E, the torque coil 2412 extends between a proximal end 2430 and a distal end 2432. The proximal end 430 is secured to a tapered portion of the core wire 2410. As illustrated in FIG. 7E, the core wire 2410 tapers from a larger diameter in a proximal zone to a smaller diameter in a distal zone 2434 with a distal transition 436 between the tapered section and the distal zone 2434 which may have a substantially constant diameter throughout. The inside diameter of the inner coil 2415 is complementary to (approximately the same as) the outside diameter at the proximal end 2430 of the core wire 2410. The tapered section of the core wire 2410 extends proximally from the distal transition 436 to a proximal transition (not illustrated) proximal to which the core wire 2410 has a constant diameter.

The torque coil 2412 may additionally be provided with a proximal radiopaque marker and/or connector such as a solder joint 2438. In the illustrated implementation, the proximal connector 2438 is in the form of an annular silver solder band, surrounding the inner coil 2415 and abutting a proximal end of the outer coil 2413.

The axial length of the torque coil 2412 may be within the range of from about 10 mm to about 50 mm and in some embodiments within the range of from about 20 mm to about 40 mm. The distal transition 2436 may be positioned within the range of from about 5 mm to about 20 mm and in some implementations within the range of from about 8 mm to about 12 mm from the proximal end of the distal cap 2420.

Referring to FIGS. 7E and 7F, the distal stopper 2414 may be provided with one or two or three or more spokes 440, extending radially outwardly from the outer coil 2413, and optionally supported by an annular hub 442 carried by the torque coil 2412. The spoke 440 may support a slider 441 having a peripheral surface 443, configured for a sliding fit within the inside diameter of the delivery catheter lumen. Preferably at least three or four or five or more spokes 440 are provided, circumferentially spaced apart equidistantly to provide rotational balance. In the illustrated embodiment, three spokes 440 are provided, spaced at approximately 120° intervals around the circumference of the torque coil 2412.

The distal stopper 2414 carries a plurality of distal surfaces 446, such as on the slider 441. The distal surface 446 is configured to slidably engage a proximal surface of a stop on the inside diameter of the delivery catheter, such as a proximally facing surface 2405 on a radially inwardly extending annular flange or ring 2402. See FIG. 7B discussed previously. This creates an interference fit with a bearing surface so that the distal stopper 2414 can rotate within the delivery catheter, and travel in an axial distal direction no farther than when distal surface 446 slidably engages the proximal surface 2405 on the stop ring 2402.

Referring to FIG. 7E, the distal end 432 of the torque coil 2412 is provided with a distal cap 2420. Distal cap 2420 may comprise an annular band such as a radiopaque marker band, bonded to the outside surface of the inner coil 2415, and axially distally adjacent or overlapping a distal end of the outer coil 2413. A proximally extending attachment such as an annular flange 2417 may be provided on the thrombus engagement tool tip 2416, for bonding to the distal cap 2420 and in the illustrated embodiment to the outer coil 2413. The distal cap 2420 may also be directly or indirectly bonded to a distal end of the core wire 2410.

The thrombus engagement tool tip 2416 is provided with a distal end 450, and a clot engagement element such as a plurality of proximally and/or radially facing engagement surfaces. In the illustrated implementation, the clot engagement element comprises a helical flange 452 that increases in diameter in the proximal direction. The flange may extend at least about one full revolution and generally less than about five or four or three revolutions about an extension of the longitudinal axis of the core wire 2410. The helical flange may be provided with a rounded, blunt edge 454, configured for slidably rotating within the tubular delivery catheter. Additional tip configurations are discussed in connection with FIGS. 8 and 9, below.

The maximum OD for the tip 2416 is generally at least about 0.005 inches and preferably at least about 0.01 inches or 0.015 inches or more smaller than the ID of the catheter aspiration lumen through which the embolism treatment system 2401 is intended to advance, measured at the axial operating location of the tip 2416 when the stopper 2414 is engaged with the stop ring. For example, a tip having a maximum OD in the range of from about 0.050-0.056 inches will be positioned within a catheter having a distal ID within the range of from about 0.068 to about 0.073 inches, and in one embodiment about 0.071 inches. With the tip centered in the lumen of the delivery (aspiration) catheter, the tip is spaced from the inside wall of the catheter by a distance in all directions of at least about 0.005 inches and in some embodiments at least about 0.007 inches or 0.010 inches or more.

Thus an unimpeded flow path is created in the annular (if centered) space between the maximum OD of the tip, and the ID of the catheter lumen. This annular flow path cooperates with the vacuum and helical tip to grab and pull obstructive material into the catheter under rotation and vacuum. The annular flow path is significantly greater than any flow path created by manufacturing tolerances in a tip configured to shear embolic material between the tip and the catheter wall.

Additional aspiration volume is obtained as a result of the helical channel defined between each two adjacent threads of the tip. A cross sectional area of the helical flow path of a tip having a maximum OD in the range of from about 0.050 to about 0.056 inches will generally be at least about 0.0003 square inches, and in some embodiments at least about 0.00035 inches or at least about 0.000375 inches. The total aspiration flow path across the helical tip is therefore the sum of the helical flow path through the tip and the annular flow path defined between the OD of the tip and the ID of the catheter lumen.

The combination of a rounded edge 454 on the thread 452 and space between the thread 452 and catheter inside wall enables aspiration both through the helical channel formed between adjacent helical threads as well as around the outside of the tip 2416 such that the assembly is configured for engaging and capturing embolic material but not shearing it between a sharp edge and the inside wall of the catheter. The axial length of the tip 2416 including the attachment sleeve 2417 is generally less than about 6 mm, and preferably less than about 4 mm or 3 mm or 2.5 mm or less depending upon desired performance.

The pitch of the thread 452 may vary generally within the range of from about 25 degrees to about 80 degrees, depending upon desired performance. Thread pitches within the range of from about 40-50 degrees may work best for hard clots, while pitches within the range of from about 50 to 70 degrees may work best for soft clots. For some implementations the pitch will be within the range of from about 40-65 degrees or about 40-50 degrees.

The tip 2416 may additionally be provided with a feature for attracting and/or enhancing adhesion of the clot to the tip. For example, a texture such as a microporous, microparticulate, nanoporous or nanoparticulate surface may be provided on the tip, either by treating the material of the tip or applying a coating. A coating of a clot attracting moiety such as a polymer or drug may be applied to the surface of the tip. For example, a roughened Polyurethane (Tecothane, Tecoflex) coating may be applied to the surface of at least the threads and optionally to the entire tip. The polyurethane may desirably be roughened such as by a solvent treatment after coating, and adhesion of the coating to the tip may be enhanced by roughening the surface of the tip prior to coating. The entire tip may comprise a homogeneous construct of any of the materials described above, or other polymeric materials, rather than just the coating.

Alternatively, the core wire 2410 may be provided with an insulating coating to allow propagation of a negative electric charge to be delivered to the tip to attract thrombus. Two conductors may extend throughout the length of the body, such as in a coaxial configuration, or a single conductor and an external grounding electrode may be used. Energy parameters and considerations are disclosed in U.S. Pat. No. 10,028,782 to Orion and US patent publication No. 2018/0116717 to Taff et al., the disclosures of each of which are hereby expressly incorporated by reference in their entireties herein. As a further alternative, the tip 2416 can be cooled to cryogenic temperatures to produce a small frozen adhesion between the tip and the thrombus. Considerations for forming small cryogenic tips for intravascular catheters are disclosed in US patent publication Nos. 2015/0112195 to Berger et al., and 2018/0116704 to Ryba et al., the disclosures of each of which are hereby expressly incorporated by reference in their entireties herein.

Figure 7G:
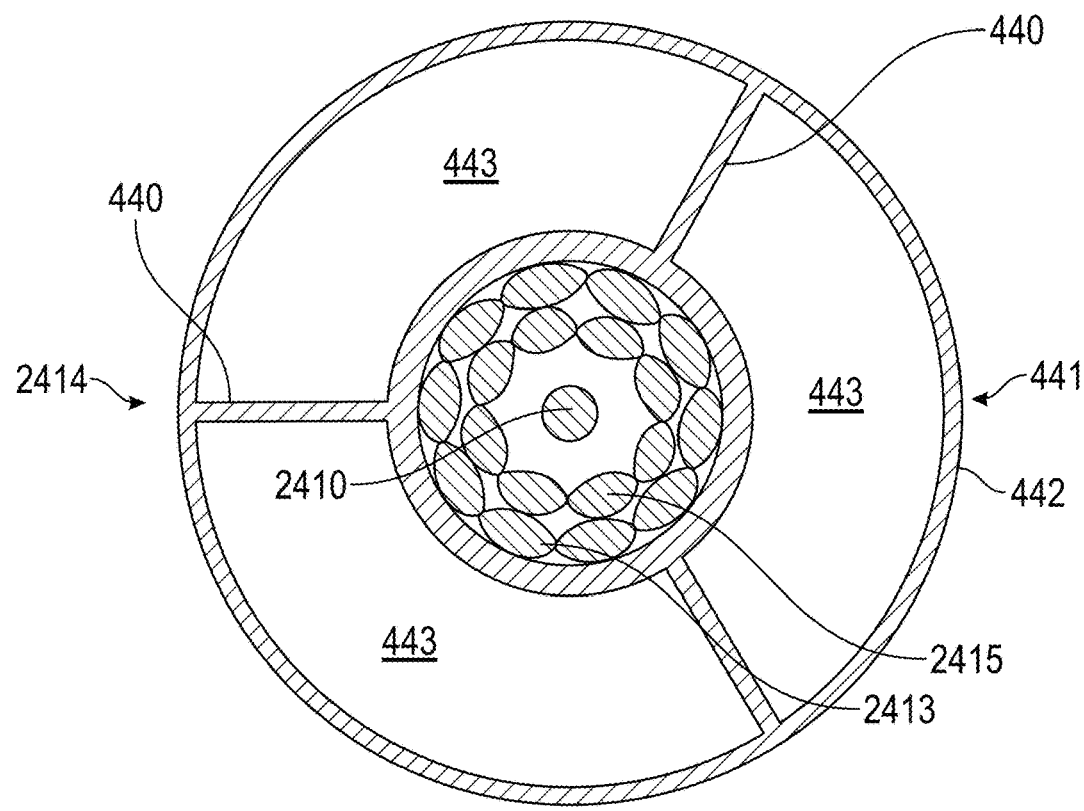
FIG. 7G is a transverse cross section through a distal stopper carried by the thrombus engagement tool.

Referring to FIG. 7G, there is illustrated a cross section through a distal stopper 2414 in which the slider 441 is a continuous circumferential wall having a continuous peripheral bearing surface 442. Three struts 440 are spaced apart to define three flow passageways 443 extending axially therethrough. The sum of the surface areas of the leading edges of the struts 440 is preferably minimized as a percentage of the sum of the surface areas of the open flow passageways 443. This allows maximum area for aspiration while still providing adequate support axially for the distal surface 446 (see FIG. 7F) to engage the complementary stop surface on the inside wall of the catheter and prevent the tip 2416 from advancing distally beyond a preset relationship with the catheter. The sum of the leading (distal facing) surface area of the struts is generally less than about 45% and typically is less than about 30% or 25% or 20% of the sum of the areas of the flow passageways 443.

In an embodiment having a torque coil 2412 with an OD of about 0.028 inches, the OD of the stopper 2414 is about 0.068 inches. The wall thickness of the struts is generally less than about 0.015 inches and typically less than about 0.010 inches and in some implementations less than about 0.008 inches or 0.005 inches or less. The struts 440 have a length in the catheter axial direction that is sufficient to support the assembly against distal travel beyond the catheter stop ring, and may be at least about 50% of the OD of the stopper 2414. In a stopper 2414 having an OD of about 0.68 inches, the struts 2440 have an axial length of at least about 0.75 mm or 0.95 mm.

Figure 7H:
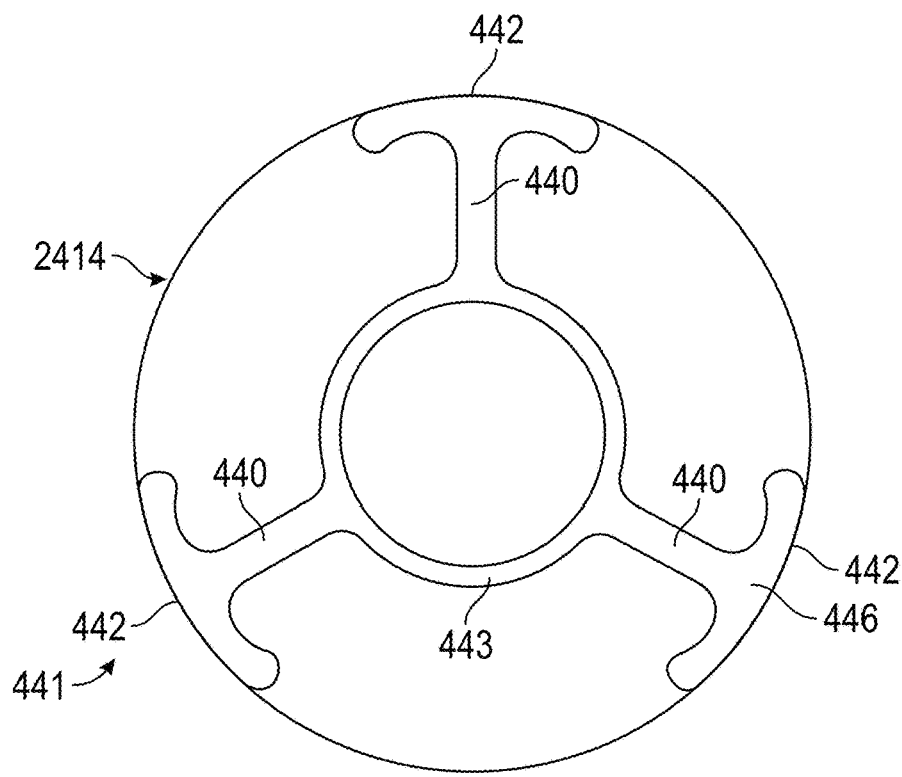
FIG. 7H is a transverse cross section through an alternative distal stopper.

Referring to FIG. 7H, there is illustrated a stopper 2414 having three distinct sliders 441 each supported by a unique strut 440. The sum of the circumference of the three peripheral surfaces is preferably no more than about 75% and in some implementations no more than about 50% or 40% of the full circumference of a continuous circumferential peripheral surface 442 as in FIG. 7G. This further increases the cross sectional area of the flow paths 443. In a catheter having an ID of no more than about 0.07 inches, an OD of the hub 443 of at least about 0.026 or 0.028 or 0.030 or more, the sum of the flow paths 443 is at least about 0.0015 inches, and preferably at least about 0.020 or 0.022 inches or more. The area of the leading edges of the struts 440 and sliders 441 is preferably less than about 0.003 inches, and preferably less than about 0.001 inches or 0.0008 inches or less. In the catheter axial direction, the length of the struts 440 is at least about 0.50 mm or 0.75 mm, and in one embodiment the length of the struts 440 and sliders 441 is about 1 mm.

Figure 8A:
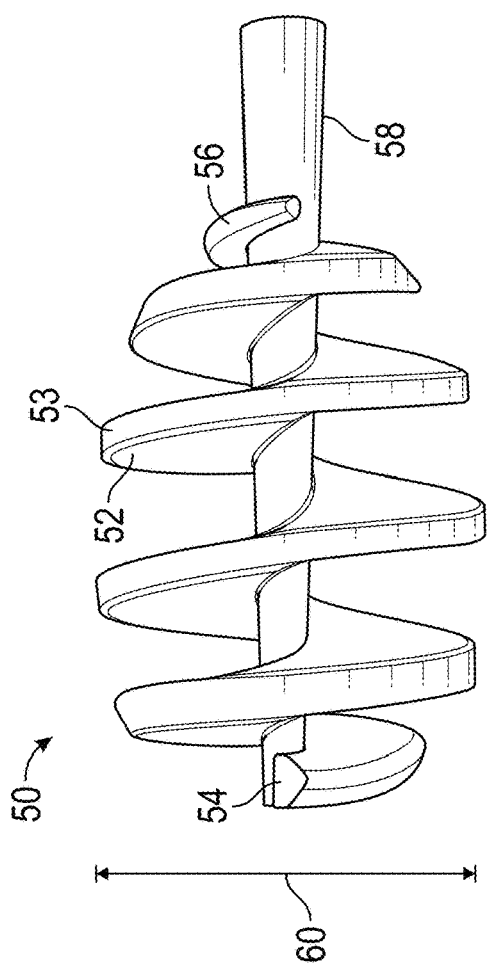

Referring to FIG. 8A, a modified distal tip 50 includes a helical thread 52 extending from a distal tip 54 to a proximal end 56 and supported by a core wire 58. The axial length of the distal tip 50 is at least about 2 mm or 5 mm or 10 mm and in some embodiments no more than about 30 mm or 20 mm measured along the core wire 58. The helical thread 52 wraps around the axis at least about 1 or 2 or 4 or more full revolutions, but in some embodiments no more than about 10 or 6 revolutions. In some embodiments the axial length along the threaded portion of the tip is within the range of from about 1 to about 8 revolutions.

The helical thread 52 on this implementation may have a constant pitch throughout its length. The pitch may be within the range of from about 10 to about 20 threads per inch, or about 5 to about 10 threads per inch depending upon desired performance. Alternatively, the thread may have multiple pitches designed to engage, transport and grasp thrombus within the catheter lumen. A distal pitch may be less than a proximal pitch. The pitch may vary continuously along the length of the thread, or may step from a first, constant pitch in a proximal zone to a second, different pitch in a distal zone of the thread. The thread 52 may comprise a continuous single helical flange, or may have a plurality of discontinuities to produce a plurality of teeth or serrations, arranged helically around the core wire.

The side elevational profile or envelope scribed by the distal tip as it rotates may have a linear or nonlinear taper on one or both ends which provide varying diameter and thus clearance along its length from the generally cylindrical ID of the catheter lumen. The maximum outer diameter 60 of the envelope (Max OD) is defined by the major diameter of the thread, and the tapers may be optimized for improved thrombus engagement and/or thrombus clearance as the helical thread element is rotated in the catheter.

Referring to FIG. 8A, the Max OD 60 in a first zone may be up to the diameter of a sliding fit within the catheter lumen, and may generally be at least about 0.015 inches or 0.010 inches smaller than the catheter lumen ID. In some implementations, the Max OD of the tip may be significantly less than the inside diameter of the catheter lumen to allow more space for the thrombus, but still create significant grasping force via engagement of the helical threads with the thrombus. In one implementation, the maximum helical thread diameter is about 0.110 inches and the catheter lumen ID is about 0.275 inches (24 F) with a 0.165 inch gap between the helical threads and catheter wall.

In the illustrated embodiment, the side elevational view profile of the helical thread OD tapers down in a proximal direction in a second zone, and tapers down in a distal direction in a third zone, such that the Max OD occurs with the central 30% or 20% or 10% of the axial length between distal tip 54 and proximal end 56.

The radial depth of the threads from the core 58 (minor diameter) to the outermost free edge 53 of the thread elements (major diameter) can be varied by varying either the major diameter as described above, as well as by varying the minor diameter (by varying the diameter of the core). The core may have a constant diameter throughout its length, or may taper, typically smaller in the distal direction as seen in FIG. 8.

The profile of the tip 50 viewed along the axis of rotation may be circular, or may vary to create a non circular pattern around the axis of rotation as seen in FIG. 9. The tip as seen in an end elevational view thus exhibits a major diameter 62 and a minor diameter 64. The minor diameter may be no more than about 95% or 90% or 80% or 70% of the major diameter, depending upon desired performance.

In certain applications, the Max OD of the tip is no more than about 35% or about 50% or about 60% of the ID of the catheter, to leave a substantial tip bypass flow path. Since this implementation does not have any centering structures, the tip will normally be pushed to one side of the aspiration lumen. When a clot becomes lodged between the tip and the opposing wall of the catheter, manual rotation of the tip can engage the clot like a worm gear and either grasp the clot (e.g., by pinning it against the opposing catheter sidewall) for retraction or facilitate freeing the blockage and aid in ingestion of the clot into the catheter.

Figure 8B:
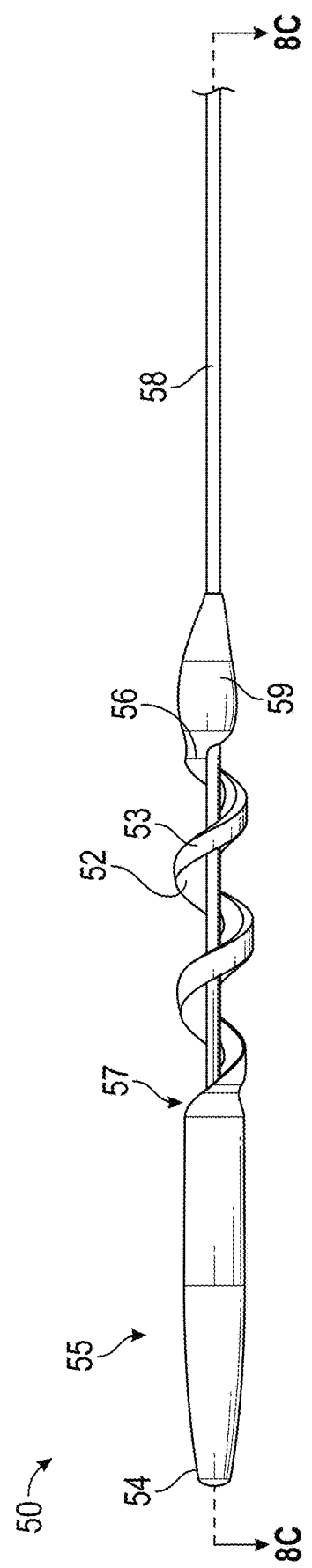

A variation of the distal tip 50 is illustrated in FIGS. 8B and 8C. The illustrated tip 50 includes a distal advance segment 55 extending between an atraumatic distal tip at 54 and a transition 57. Helical thread 52 extends proximally from transition 57 to a proximal end 56 of the helical thread 52. A trailing segment 59 extends between the proximal end 56 of the thread and the proximal end of the tip. The thread may be inclined in a proximal direction, to produce a proximally facing undercut and a distal surface that inclines radially outwardly in a proximal direction.

The axial length of the advance segment 55 may be at least about 1 cm or 2 cm and in some implementations is within the range of from about 2 cm to about 4 cm. The axial length of the helical thread 52 along the longitudinal axis is typically within the range of from about 1 cm to about 5 cm and in certain implementations between about 2 cm and 3 cm.

The outside diameter of the advance segment 55 at distal tip 54 is generally less than about 0.024 inches, or less than about 0.020 inches and, in one implementation, is about 0.018 inches. The maximum outside diameter of the advance segment 55 and helical thread 52 may be within the range from about 0.020 to about 0.050 inches, and, in one implementation, is less than about 0.040 inches, such as about 0.035 inches. The advance segment, helical thread and trailing segment of the tip 50 may be molded over the core wire 58 using any of a variety of polymers known in the catheter arts.

Referring to FIG. 8C, a first radiopaque marker 63 may be carried on the core wire 58 beneath the advance segment 55. A second radiopaque marker 65 may be carried on the core wire 58 within the trailing segment 59. Each radiopaque marker may comprise a coil of radiopaque wire such as a platinum iridium alloy wire having a diameter about 0.002 inches, and wrapped around the core wire 58 and soldered to the core wire 58 to produce an RO coil having an outside coil diameter of less than about 0.020 inches, such as about 0.012 inches. The radiopaque markers may also function as an axial interference fit between the core wire 58 and the molded advance segment 55 and trailing segment 59 to resist core wire pull out from the tip 50.

In one implementation, the maximum OD of the thread 52 exceeds the maximum OD of the advance segment 55 by at least about 15% or 25% or 30% or more of the OD of the advance segment 55, to facilitate crossing the clot with the advance segment 55 and engaging the clot with the thread. The thread pitch may be within the range of from about 0.75 to about 0.30, or within the range of from about 0.10 and about 0.20, such as about 0.14 inches.

Preferably, the maximum OD of the tip 50 is less than about 60% or 50% of the aspiration catheter ID, and may be within the range of from about 35% to about 55% of the catheter ID. In certain implementations, the maximum OD of the tip 50 may be within the range of from about 0.044 inches to about 0.050 inches within a catheter having an ID within the range from about 0.068 inches to about 0.073 inches.

For this configuration of the tip 50, the distal stop on the proximal end of the core wire 58 is configured to permit distal advance of the tip 50 such that the distal end 54 may be advanced at least about 2 to 3 cm and preferably as much as 4 to 8 cm beyond the distal end of the catheter. In one implementation, the distal stop limits distal advance of the tip 50 so that the proximal end is within two or within one or than 0.5 cm in either the distal or proximal direction from the distal end of the aspiration catheter.

Figure 10:
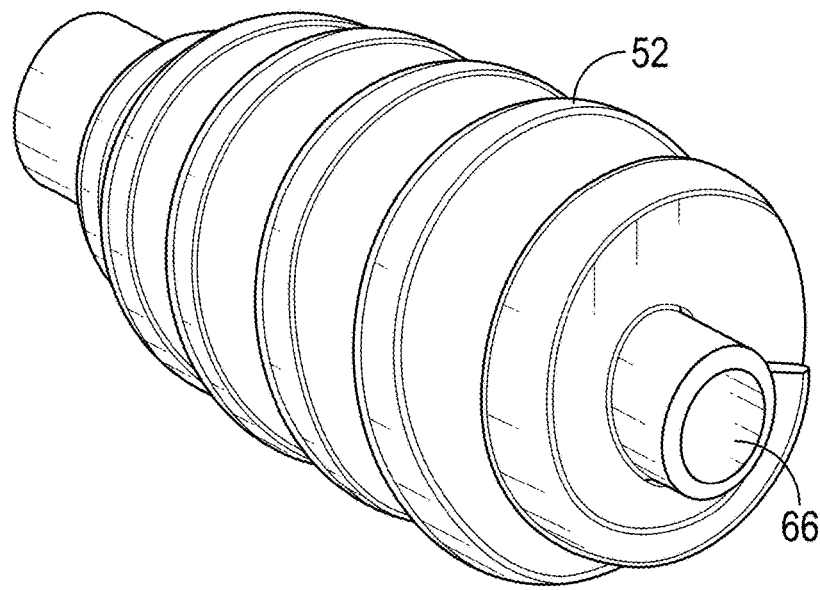
FIG. 10 is an end perspective view of a cannulated helical tip element with a lumen for a guidewire or other devices or infusion or aspiration of fluids.

Referring to FIG. 10, the helical tip element may be part of an over-the-wire structure which can be moved over a guide wire. This structure allows the guide wire to be positioned and the helical tipped structure can be inserted with a surrounding catheter, or independently into a surrounding catheter which is already in place and over the guidewire. The helical tip structure can be rotated freely around the guide wire. The lumen 66 may be used for a guide wire or other devices or fluids to communicate from proximal end of the torque member through the distal tip of the helical tip element.

Figure 11:
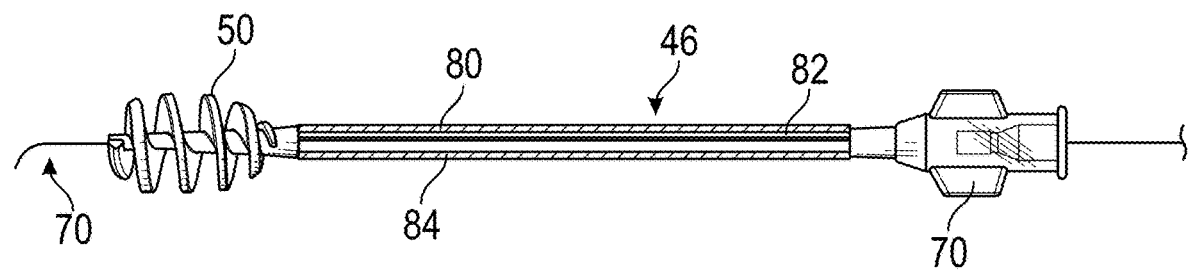
FIG. 11 is a schematic side elevational view of an over the wire helical tipped structure.

FIG. 11 illustrates one embodiment of an over-the-wire helical tipped engagement wire 46 with a central lumen having guidewire 70 extending therethrough. Similar to other helical tip structures disclosed therein, this is intended to operate within a coaxial surrounding catheter as has been previously discussed. As with implementations discussed elsewhere herein, engagement wire 46 includes an elongate flexible body configured to transmit torque between a proximal hub or handle 70 and the distal tip 50. The body may comprise a torque coil construction as disclosed elsewhere herein, having two or more concentric coils typically wound in a reverse direction from the adjacent coil. The engagement wire 46 optionally includes an axially extending longitudinal stabilizer 82. Preferably, the torque coil is enclosed within a polymeric jacket such as a shrink wrap tube.

Figure 12:
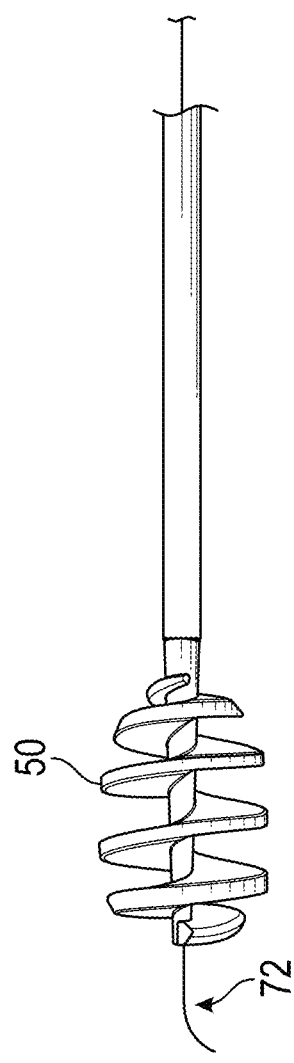
FIG. 12 is a schematic side elevational view of a helical tipped structure with a fixed guide wire tip.

The helical tip may alternatively have a fixed guide wire 72 distal advance segment extending from the distal end of the helical tip (See FIG. 12) or a polymeric distal extension to provide an atraumatic tip (See FIG. 8B). This fixed guide wire advance segment is typically easily bent when interacting with the patient's anatomy to avoid injuring tissue. The fixed guide wire advance segment may be between about 1 cm and about 10 cm but may be shorter or longer depending on the application.

In accordance with another aspect of the invention, a catheter dilator sheath assembly is provided to enable easy, safe, and efficient tracking of a large diameter catheter or catheter system from insertion into a large peripheral blood vessel and advanced to the target location of interest. The large diameter catheter, such as for aspiration or other mechanical means of removal of embolus or thrombus from large vessels, has a diameter within the range from about 8 F (0.105") to about 24 F (0.315").

Figure 13:
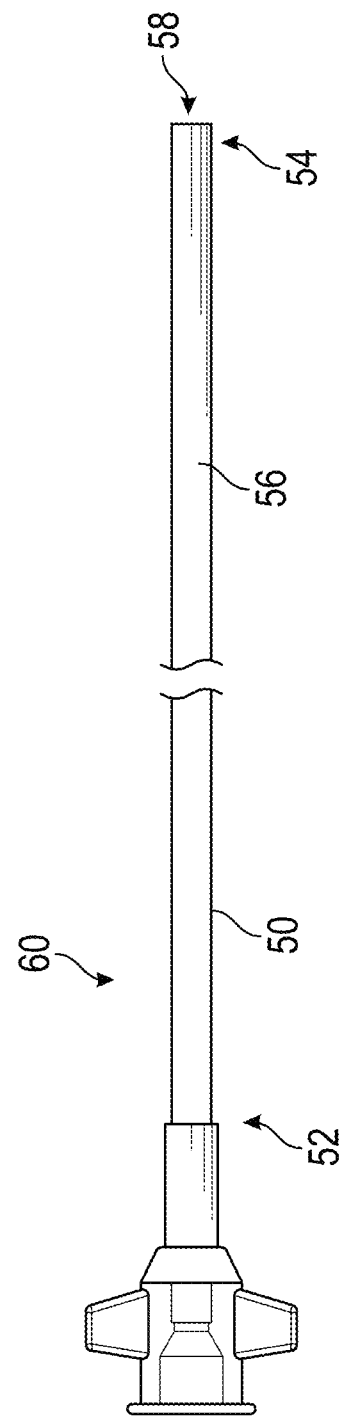
FIG. 13 is a side elevational view of a large bore catheter.
Figure 14:
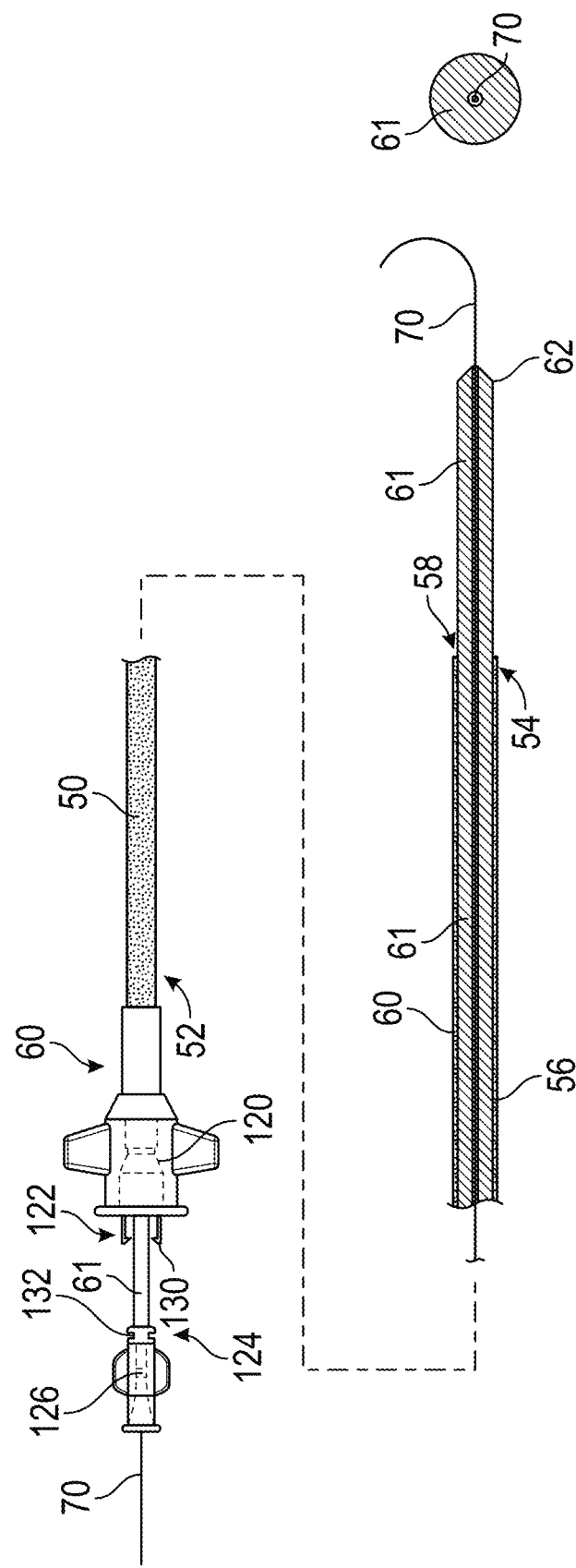
FIG. 14 is a side elevational partial cross section of the catheter of FIG. 13, having a cannulated guide rail extending therethrough over a guidewire.

Referring to FIGS. 6 and 13, one implementation of the catheter 60 includes an elongate flexible tubular body 50, having a proximal end 52, a distal end 54 and a side wall 56 defining a central lumen 58. Referring to FIG. 14, an elongate flexible cannulated rail or dilator 61 is shown extending over the guidewire 70 and occupying the space between the guidewire 70 and the large inside diameter of the central lumen 58 of the large diameter catheter 60 to provide support to the catheter and/or an atraumatic tip during delivery.

This catheter-cannulated rail-guidewire assembly is intended to easily track through anatomical challenges more easily than the catheter. The catheter-rail-guidewire assembly then acts as a first stage of the catheter delivery system and enables the large diameter catheter or catheter system to be inserted and independently advanced over this first stage into a blood vessel (e.g. the femoral vein) percutaneously over a guidewire and advanced through potentially tortuous vasculature to the remote target location of interest without requiring advanced skills or causing kinking of the catheter.

The cannulated rail 61 may comprise a soft flexible cylindrical body having a guidewire lumen with a diameter of no more than about 0.040" and an outside diameter no greater than about 0.025" or about 0.010" smaller than the inner diameter of the large diameter catheter. Thus the wall thickness of the cannulated rail 61 is typically at least about 0.010" less than the radius of the large diameter catheter and in some implementations at least about 0.120" or more, depending upon the size of the annular space between the inside diameter of the catheter and the outside diameter of the guidewire. Depending upon the ID of the access catheter, the rail 61 may have a wall thickness of at least about 0.05 inches, at least about 0.075 inches, at least about 0.100 inches and in some implementations at least about 0.12 inches. The wall thickness of the rail may exceed the inside diameter of the guidewire lumen.

The cannulated rail 61 may have an elongated advance segment having a tapered distal tip 62 that may project beyond the distal end 54 of the catheter 60. The thick sidewall of the cannulated rail 61 may comprise one or more flexible polymers, and may have one or more embedded column strength enhancing features such as axially extending wires, metal or polymeric woven or braided sleeve or a metal tube, depending upon the desired pushability and tracking performance along the length of the dilator.

Optionally, the proximal segment of the rail or dilator which is not intended to extend out of the distal end of the catheter may be a structure which is not coaxial with the guidewire, but is instead a control wire which extends alongside the guidewire in the catheter and allows the distal tubular telescoping segment of the rail or dilator to be retracted or extended. (analogous to rapid exchange catheters) without the entire length of the rail structure being over the wire. This allows removal or insertion of the rail or dilator over a shorter guidewire because of the shorter coaxial segment tracking over the guidewire. The distal tubular segment may have a length of no more than about 40 cm or 30 cm or less, carried by a proximally extending control wire.

Catheter 60 may be provided with a proximal hub 120, having a port for axially movably receiving the rail 61 therethrough. The hub 120 may be provided with an engagement structure such as a first connector 122 for releasably engaging a second complementary connector 124 on a hub 126 on the proximal end of the rail 61. First connector 122 may comprise an interference structure such as at least one radially moveable projection 130, for releasably engaging a complementary engagement structure such as a recess 132 (e.g., an annular ridge or groove) on the hub 126. Distal advance of the rail 61 into the catheter 60 causes the projection 130 to snap fit into the recess 132, axially locking the catheter 60 and rail 61 together so that they may be manipulated as a unit.

The dilator is inserted through the hemostasis valve in the hub 120 of a large bore (e.g., 24 F) catheter 60 and advanced through the catheter until the retention clip on the dilator hub 126 or catheter hub 120 snaps into the complementary recess on the other hub. In this engaged configuration, the flexible distal end of the 24 F rail dilator 61 will extend at least about 5 cm or 10 cm, and in some implementations at least about 15 cm or 20 cm beyond the distal end 54 of the 24 F catheter 60. The rail dilator and 24 F catheter system are thereafter distally advanced over a previously placed guidewire and into the introducer sheath.

The dilator and catheter combination of the present invention differentiate over prior systems both because of the flexibility of a distal zone of the dilator and greater length of the dilator than the corresponding catheter. Typically, a dilator is a uniform stiffness and length-matched to its catheter, with only a short atraumatic tip of the dilator extending beyond the distal end of the catheter. The dilator of the present invention has a supportive proximal end and a flexible distal end, with a total dilator length much longer than the catheter 60 to enable, as an example, the following procedure.

In use, a guidewire 70 such as an 0.035" guidewire is advanced under fluoroscopy using conventional techniques into a selected vessel. The cannulated rail 61, optionally with the catheter 60 mounted thereon, is loaded over the proximal end of the guidewire 70 and advanced distally over the wire until the distal end of the rail is in position at the target site.

The 24 F catheter 60 is thereafter unlocked from the rail 61 and advanced over the rail 61 to the desired site, supported by the rail 61 and guidewire 70 combination. Because the uncovered advance section of the rail has already traversed the challenging tortuosity through the heart, the catheter 61 now just slides over the advance section of the rail for easy passage to the final target location. The supportive proximal zone and flexible distal advance section of the rail enables ease of delivery through the most challenging anatomy in, for example, a PE procedure going from the vena cava through the tricuspid and pulmonary valves of the heart into the central pulmonary artery without concern about damaging the tissue (atraumatic, flexible tip) or damaging the dilator (high kink resistance due to flexible, high wall thickness "solid" dilator construction).

The cannulated rail 61, or the cannulated rail 61 and the guidewire 70 combination, may thereafter be proximally withdrawn, leaving the large bore catheter 60 in position to direct a procedure catheter such as any of the aspiration catheters disclosed elsewhere herein to the target site.

Figure 15:
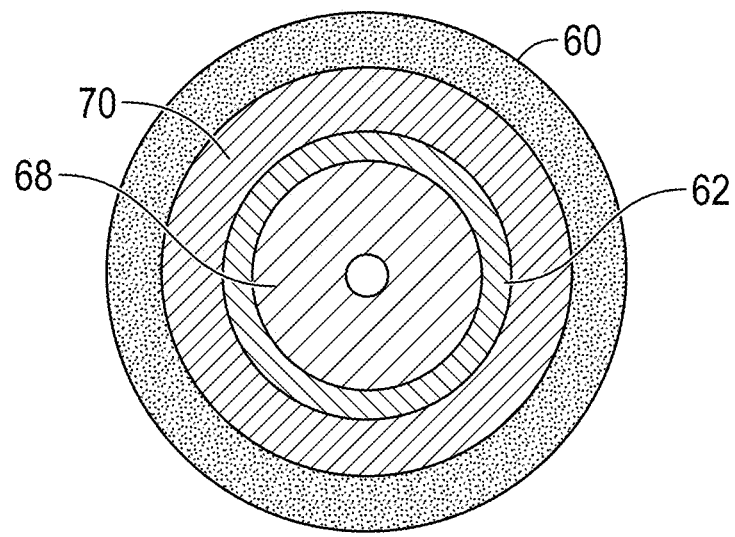
FIG. 15 is a cross sectional view through a dual dilator system such as that shown in FIG. 16.
Figure 16:
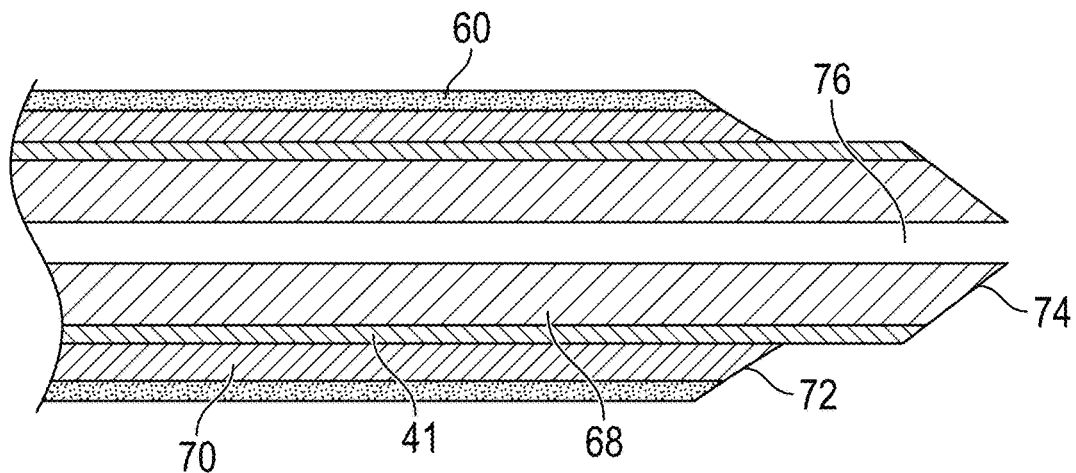
FIG. 16 is a side elevational cross section of a distal portion of a dual dilator system of the present invention.

Referring to FIG. 15, the large diameter (LD) catheter 60 may in some situations have a smaller diameter (SD) catheter though its central lumen for the purposes of introducing an additional functionality (e.g., clot grabber catheter 62, imaging catheter 10, or mechanical thrombectomy tool 66) and/or telescoping the SD catheter to more distal locations in the anatomy. In order to enable delivery of the LD catheter 60 and SD catheter as a single system, the SD catheter may have a core dilator 68 for support, and the gap between the outer diameter of the SD catheter and inner diameter of the LD catheter 60 may be maintained or supported by a second, tubular dilator 71. The tubular dilator 71 may have a shaped distal tip 72 for a smooth tapered transition from the SD catheter 41 to the LD catheter 40. The distal end 34 of the core dilator may be provided with a complementary taper to the distal taper of the thin wall SD dilator (FIG. 16) or may end at the distal end of the LD catheter (FIG. 17).

The core dilator 68 inside the SD catheter 41 and tubular dilator 70 between the two catheters may have an interlocking feature to create a single (SD+LD) catheter+(core+tubular) dilator system. For example, complementary connectors may be provided on hubs on the proximal ends of the system components.

Figure 17:
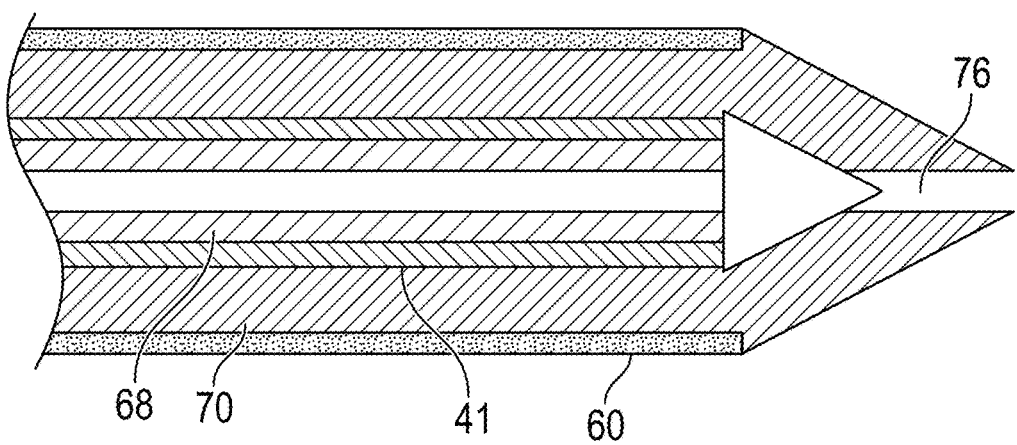
FIG. 17 is a cross section as in FIG. 16, with a distal tip formed by the tubular dilator.

Referring to FIG. 17, the tip of the tubular dilator 70 may be configured to taper to the guidewire lumen 76, thus covering and extending distally beyond the small diameter catheter 41 if it is in place. The tip of the tubular dilator 70 may be provided with a longitudinally extending slit 78, scored or perforated one or more times to allow the tip to split longitudinally and be pulled back into the space between the LD and SD catheters and fully expose the distal end of the small diameter catheter 41. See FIG. 18.

Figure 18:
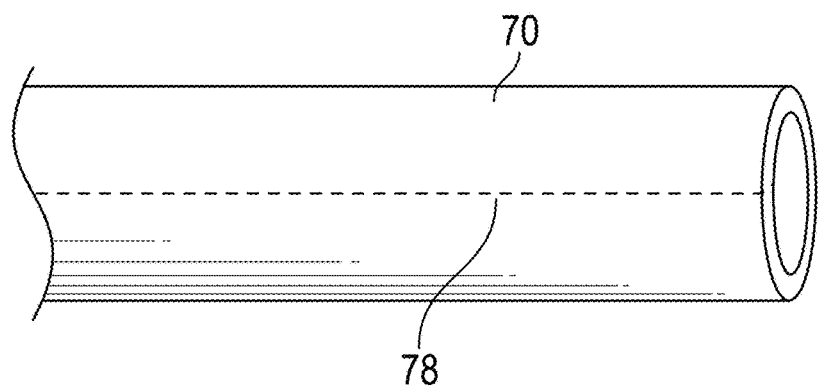
FIG. 18 is a side elevational view of a portion of a tubular dilator having a separation line to allow longitudinal splitting of the sidewall during proximal retraction from the system.

The single (SD+LD) catheter+(core+tubular) dilator system may be pre-assembled and detachably interlocked at the proximal hub. Additional tubular dilators having a series of outside diameters and wall thicknesses may be provided such that the SD catheter may be used in combination with different diameter LD catheters. A LD catheter may be used with different SD catheters by providing tubular dilators having the same OD but a series of different inside diameters. The core+tubular dilators may simply be pulled proximally to withdraw both dilators as a single system, or the tubular dilator may be configured with a tab or handle at the proximal end and a slit, scoring, perforation or other mechanism so as to split, peel, or tear it along the longitudinal axis during withdrawal to allow the tubular dilator to peel from the SD catheter as it slides proximally out of the space between the LD and SD catheters (FIG. 18).

Any of the thrombectomy catheters disclosed herein may be provided with a surface configuration on the inside surface of the central lumen to affect the behavior of clot drawn into the lumen. In general, the catheter, with diameter within the range from about 8 F (0.105") to about 24 F (0.315"), includes an elongate flexible tubular body, having a proximal end, a distal end and a side wall defining a central lumen. The access or evacuation catheters may also include a rotatable core wire or other apparatus that extends though the catheter lumen for the purposes of engaging thrombus at the distal end of the catheter as has been discussed.

The central lumen 90 is defined by an inside surface 100 of the tubular body 104, which in some embodiments is a smooth cylindrical surface. However, referring to FIGS. 19A and 19B, the inner surface 100 of at least a distal zone 102 of the tubular body 104 may be provided with a surface configuration to engage thrombus and limit unrestricted sliding of the thrombus along the inner surface 100. The distal zone 102 may have an axial length within the range of from about 0.5" to about 12" or more, depending upon desired performance and/or manufacturing technique.

Figure 19A:
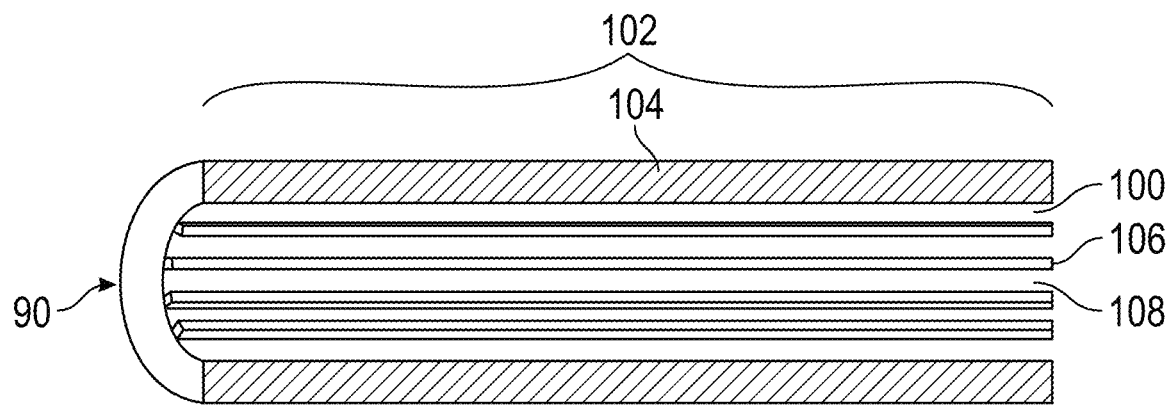
FIG. 19A is a longitudinal cross-sectional view through a distal zone of a catheter, having axially extending surface structures on the inside surface of the catheter wall.

For example, referring to FIG. 19A, at least one or five or ten or more axially extending surface structures such as radially inwardly extending ridges 106 separated by grooves 108 may be provided to facilitate proximal ingestion of the thrombus and/or to engage thrombus and resist rotation of the thrombus within the lumen when the core wire or other thrombus grabbing apparatus is rotated within the lumen.

The corrugation pattern may also increase the transport of the thrombus proximally by decreasing the surface area of contact between the thrombus and the inside surface of the tubular body. The spacing circumferentially may be regular or irregular, and the crest and trough pattern, dimensions and distribution may be varied. Examples of trough cross sections include the illustrated rectangular, semicircular or triangular, among others.

Figure 19B:
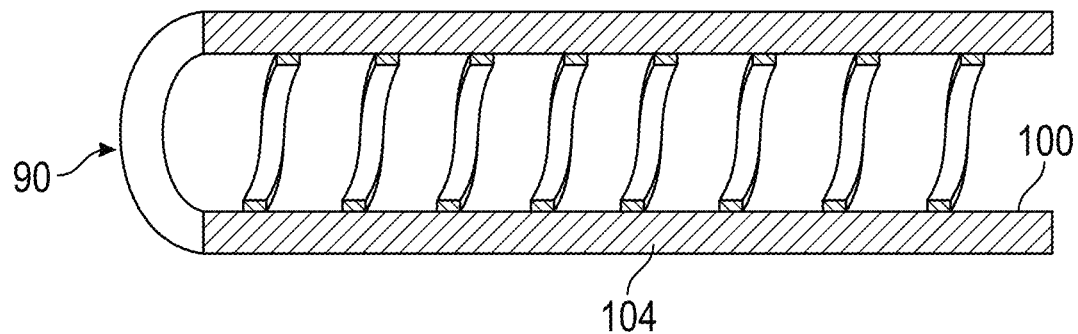
FIG. 19B is a longitudinal cross-sectional view as in FIG. 19A, having helical surface structures on the inside surface of the catheter wall.
Figure 20:
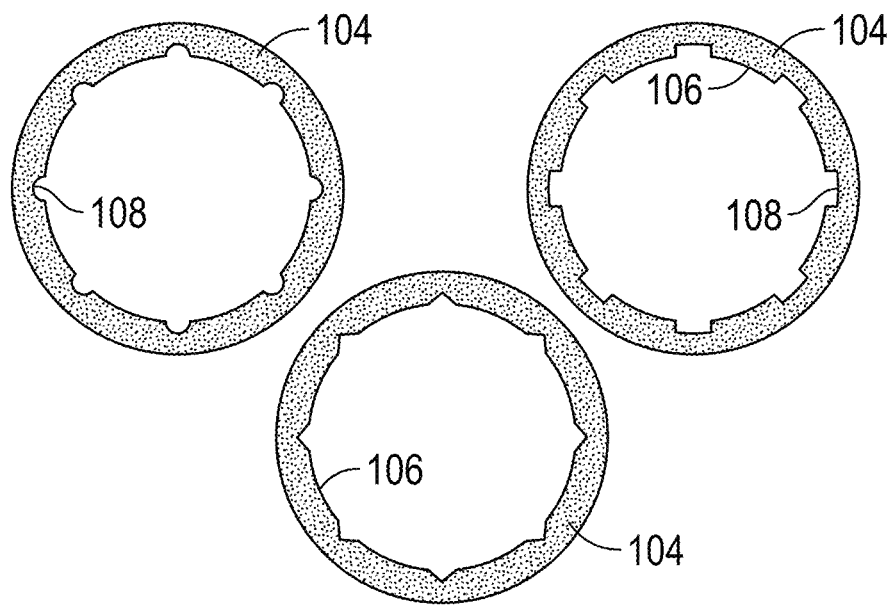
FIG. 20 illustrates transverse cross-sectional views through the catheter of FIG. 19A, showing different ridge and groove configurations.

In one implementation illustrated in FIG. 19B, the surface discontinuity, i.e. grooves or ridges, may extend in a circumferential (e.g. helical) configuration having a constant or variable pitch along the length of the distal zone 102. The helical guide may spiral in a first direction in order to oppose rotation of the core wire or other apparatus in a second direction, or in the same direction to cooperate with the rotation of the core wire in order to facilitate thrombus ingestion proximally into the catheter. The grooves or ridges may have a curved profile or generally rectilinear, having generally flat or cylindrical side walls.

In another embodiment, the inner surface 100 of the distal zone 102 of the tubular body 104 may have a three-dimensional pattern that reduce friction of the thrombus moving proximally in the catheter and create resistance to the thrombus moving distally in the catheter after it has been ingested into the catheter. This pattern may be regular throughout or in the distal end of the tubular body, or irregular and decrease gradually and progressively in density, pattern, or geometry along the length of the catheter or the distal section. This pattern may also be provided in combination with lubricious coatings or surfaces.

Figure 21:
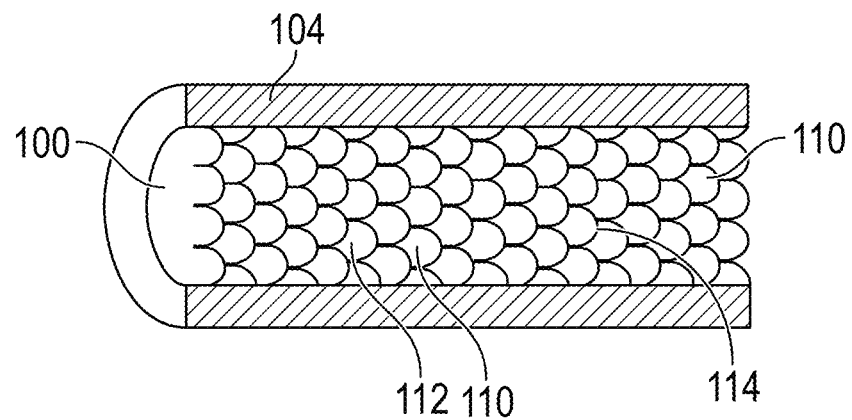
FIG. 21 illustrates an inside surface of a catheter wall having differential friction surface structures for facilitating proximal movement of thrombus and inhibiting distal movement of thrombus.

The three-dimensional differential friction pattern may be defined by a regular or irregular pattern of protuberances 110 or depressions on the inner surface of the catheter, each of which presents an exposed face 112 inclined radially inwardly in the proximal direction, with each inclined exposed face 112 terminating proximally in a proximally facing engagement surface such as a dropoff edge 114, which may be curved in an axial direction as shown in FIG. 21 to provide a ratchet or fish scale type of configuration.

The scales may flex, hinge or pivot at the distal end, which will not impact the proximal ingestion of the thrombus, but will create additional resistance to the thrombus moving distally in the catheter after it has been ingested into the catheter.

In alternative embodiments, the differential friction surface structures on the inner surface of the distal zone may be relatively shallow convex or concave "dimples" or other regular or irregular surface discontinuities that are generally triangular, oval, oblong arcs, serpentine shapes or a plurality of angled fibers that incline radially inwardly in a proximal direction.

Figure 22:
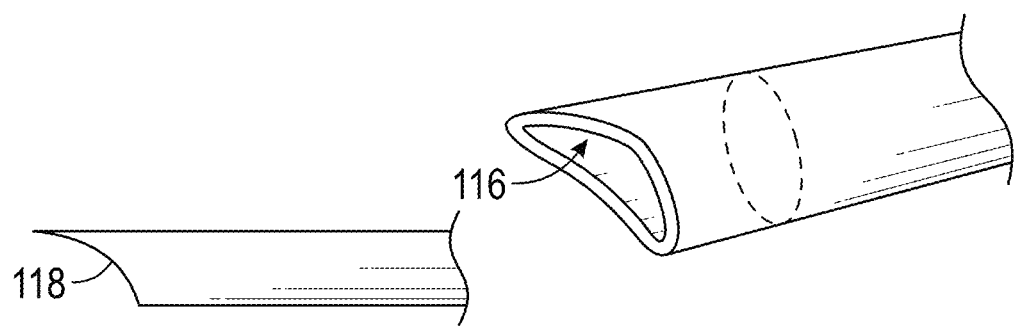
FIG. 22 shows an angled distal catheter tip.

Referring to FIG. 22, the lumen 116 of the tubular body may be non-cylindrical and instead be oval or other geometry lacking rotational symmetry and containing a minor axis which is less than a major axis due to one or more longitudinal deformations of the lumen. These longitudinal deformations of at least the inner surface of the tubular body serve as structures to increase the rotational resistance to thrombus or embolic matter in the lumen. These deformations may contain their own lumens within the wall of the tubular body for pull wires of a steerable tip or to deliver fluids or to measure pressure or to transmit a vacuum or other functions.

The distal end 118 of the tubular body may be angled such that the distal face of the catheter resides on a plane or a curve with an end to end secant that crosses the longitudinal axis of the tubular body at an angle within the range from about 30 degrees to about 60 degrees. The distal face of the angled tip may be non-planar and may include one or two or more inflection points or curves. This angled tip may improve catheter navigation and thrombus ingestion by providing more surface area for engagement between the catheter and the thrombus. (see, e.g., FIG. 31D and associated description in US publication No. 2020/0001046 A1 to Yang, et al., which is hereby incorporated in its entirety herein by reference.)

The opening at the distal end of the tubular body may be expandable from a first inside diameter for transluminal navigation to a second, larger inside diameter providing a funnel like tip with an enlarged distal opening to facilitate aspiration of thrombus into the lumen. The diameter at the distal opening of the fully open funnel exceeds the diameter of the cylindrical distal end of the tubular body by at least about 5% or 10% or more. (see FIGS. 4A-4I and associated description in U.S. Pat. No. 10,441,745 to Yang, et al., which is hereby incorporated in its entirety herein by reference.)

The distal end of the catheter may have an increasing inner diameter while maintaining a constant outer diameter, representing a tapered distal wall, or the inner and outer diameters may both increase, representing a conical funnel like tip.

The funnel tip is may be made of a material that is rigid enough to maintain structural integrity under aspiration and flexible enough that it may deform to accommodate and enable thrombus across a range of size, shape, and maturity to be aspirated into the catheter lumen.

The funnel tip may telescope out of the thrombectomy catheter. A hollow cylindrical structure at the end of a long, flexible hypo tube or at the end of two or more stiff wires may be advanced through the catheter, and when the hollow cylindrical structure extends beyond the distal catheter tip and its associated circumferential constraint, the structure expands into a conical funnel shape. Additional details of these features may be found in U.S. Pat. No. 10,441,745 to Yang, et al., previously incorporated in its entirety herein by reference.)

The thrombectomy catheter with inner lumen features to enhance the extraction of thrombus and/or distal end features may enable easier, more efficient removal of a broad spectrum of thrombus size, shapes, and maturity from vascular conduits including the pulmonary arteries, resulting in shorter procedure times and a lower total volume of blood loss. This is achieved by promoting proximal movement of the thrombus while creating resistance to the thrombus moving distally in the catheter after it has been ingested into the distal catheter.

The foregoing inventions and improvements will enable the engagement and capture of a very wide range of thrombus, from acute to mature in nature, thus enabling the extraction of the thrombus from the blood vessel in which it may be impeding blood flow. Additionally, the configurations described above enhance safety by reducing the risk of vascular tissue injury due to mechanical engagement of the helical tip element and/or catheter tip with the vessel wall.

In the foregoing description, similar features in different drawings are sometimes identified by slightly differing terminology. This is not intended to imply differences that do not exist. Slightly different features are illustrated in different drawings, and those of skill in the art will recognize that any of the features disclosed here in can be re-combined with any of the catheters or other structures disclosed here in.

What is claimed is:

1. A system for accessing a pulmonary artery, comprising:
   an elongate, flexible tubular access catheter, having a proximal end, a distal end, and an access catheter hub on the proximal end;
   an elongate, flexible rail, having a proximal end, a distal advance segment, and a rail hub on the proximal end;
   an engagement structure on the access catheter hub, configured to releasably engage a complementary engagement structure on the rail hub;
   a thrombus evacuation catheter configured to extend through the access catheter; and
   a thrombus engagement tool configured to extend through the thrombus evacuation catheter, wherein the thrombus engagement tool comprises an elongate flexible body having a thrombus engagement tip with a helical thread,
   wherein the distal advance segment of the rail extends at least 5 cm beyond the distal end of the access catheter when the access catheter hub is adjacent the rail hub.

2. A system as in claim 1, wherein the distal advance segment of the rail extends at least about 15 cm beyond the distal end of the access catheter when the access catheter hub is adjacent the rail hub.

3. A system as in claim 1, wherein the rail increases in flexibility in a distal direction.

4. A system as in claim 3, wherein the rail comprises a proximal segment separated from the distal advance segment by a transition.

5. A system as in claim 4, wherein the distal advance segment has a greater flexibility than the proximal segment.

6. A system as in claim 1, wherein the rail comprises a guidewire lumen.

7. A system as in claim 6, wherein the guidewire lumen can accommodate a guidewire having a diameter of no greater than about 0.035", the catheter is at least about 20 French, and the rail has an outside diameter that is no more than about 0.025" smaller than the inside diameter of the access catheter.

8. A system as in claim 6, wherein a wall of the rail has a the wall thickness of at least about 0.05 inches.

9. A system as in claim 6, wherein a wall of the rail has a wall thickness of at least about 0.10 inches.

10. A system as in claim 1, wherein the access catheter hub comprises a hemostasis valve.

11. A system as in claim 1, wherein the access catheter hub comprises a projection configured to snap fit into a recess on the rail hub.

12. A system as in claim 1, wherein the access catheter is at least about 8 French.

13. A system as in claim 1, wherein the access catheter is at least about 20 French.

14. A system as in claim 1, wherein the thread extends from about two to about 10 revolutions around the elongate flexible body.

15. A system as in claim 14, wherein the thread has a maximum diameter that is no more than about 60% of an inside diameter of an adjacent portion of the thrombus evacuation catheter.

16. A system as in claim 1, further comprising a handle on the proximal end of the thrombus engagement tool configured to permit manual rotation of the thrombus engagement tool.

* * * * *

UNITED STATES PATENT AND TRADEMARK OFFICE
CERTIFICATE OF CORRECTION

| | | |
|---|---|---|
| PATENT NO. | : 11,253,277 B2 | Page 1 of 1 |
| APPLICATION NO. | : 17/125743 | |
| DATED | : February 22, 2022 | |
| INVENTOR(S) | : Michael Buck et al. | |

It is certified that error appears in the above-identified patent and that said Letters Patent is hereby corrected as shown below:

In the Specification

In Column 24, Line 16, delete "FIGS. 4A-4I" and insert --FIGS. 4A-4I--.

In Column 24, Line 40, delete "reference.)" and insert --reference.--.

In the Claims

In Column 26, Claim 8, Line 8, delete "a the" and insert --a--.

Signed and Sealed this
Twenty-fourth Day of May, 2022

Katherine Kelly Vidal
*Director of the United States Patent and Trademark Office*